(12) United States Patent
Kaskoun et al.

(10) Patent No.: US 9,615,794 B2
(45) Date of Patent: Apr. 11, 2017

(54) METHOD, DEVICES AND SYSTEMS FOR SENSOR WITH REMOVABLE NODES

(71) Applicant: QUALCOMM Incorporated, San Diego, CA (US)

(72) Inventors: Kenneth Kaskoun, La Jolla, CA (US); Brian David Niznik, San Diego, CA (US); Michael David Atella, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 434 days.

(21) Appl. No.: 14/094,860

(22) Filed: Dec. 3, 2013

(65) Prior Publication Data

US 2015/0150505 A1 Jun. 4, 2015

(51) Int. Cl.
*A61B 5/00* (2006.01)
*A61B 5/11* (2006.01)

(52) U.S. Cl.
CPC .......... *A61B 5/6833* (2013.01); *A61B 5/0002* (2013.01); *A61B 5/11* (2013.01); *A61B 5/1112* (2013.01); *A61B 5/684* (2013.01); *A61B 5/742* (2013.01); *A61B 5/7405* (2013.01)

(58) Field of Classification Search
CPC .............................. A61B 5/6833; A61B 5/684
See application file for complete search history.

(56) References Cited

U.S. PATENT DOCUMENTS

| | | | |
|---|---|---|---|
| 2009/0054737 A1 | 2/2009 | Magar et al. | |
| 2011/0015496 A1* | 1/2011 | Sherman | A61B 5/0006 600/301 |
| 2012/0071731 A1 | 3/2012 | Gottesman | |
| 2013/0191513 A1 | 7/2013 | Kamen et al. | |
| 2015/0073285 A1* | 3/2015 | Albert | A61B 5/0408 600/509 |
| 2016/0324472 A1 | 11/2016 | Kaskoun et al. | |

OTHER PUBLICATIONS

Chi Y.M., et al., "Wireless Non-contact EEG/ECG Electrodes for Body Sensor Networks," International Conference on Body Sensor Networks (BSN), 2010, pp. 297-301.

(Continued)

*Primary Examiner* — Eric D. Bertram
(74) *Attorney, Agent, or Firm* — Kilpatrick Townsend & Stockton

(57) ABSTRACT

An integrated adhesive sensor array includes an adhesive a patch, a sensor hub, and a detachable sensor pod packaged as a unit. The patch may include a docking area for the detachable sensor pod. The detachable sensor pod may include at least one sensor and may be configured to be detached from the patch and applied to various locations on a body. The detachable sensor pod may send sensor data to the sensor hub via a wired link when on the patch and via a wireless link when detached from the patch. The sensor hub receives sensor data from the detachable sensor pod and relays the data to a receiver. The sensor hub and detachable sensor pod may include indicators for communicating information. The sensor hub may include a power source for powering the sensor hub and a detachable sensor pod attached to the main sensor unit or patch.

9 Claims, 11 Drawing Sheets

(56) References Cited

OTHER PUBLICATIONS

Ling C.E., et al., "Design Requirement Clarification for Body Area Network (BAN)," Apr. 2011, 114 Pages.
Ngoc T.V., "Medical Applications of Wireless Networks," < URL : http://www.cse.wustl.edu/~jain/cse574-0B/ftp/medical/ >, Apr. 21, 2008, 12 Pages.
International Search Report and Written Opinion—PCT/US2014/067416—ISA/EPO—Feb. 9, 2015.

* cited by examiner

METHOD, DEVICES AND SYSTEMS FOR SENSOR WITH REMOVABLE NODES

BACKGROUND

Adhesive "peel off" sensors are becoming popular for biometric and biomedical monitoring. In examples, a wireless adhesive sensor may be applied to a body portion of a patient and may measure various biometric quantities. While wireless sensors provide some degree of convenience, challenges remain.

Challenges in implementing wearable sensors include reliability, connection quality, data security, integrity and fault tolerance, integration of diverse sensor technology, managing delay of real-time measurements, comfort, longevity and other challenges. In view of these challenges, disadvantages for existing sensors and sensor networks are numerous. Existing wireless sensors may be large, have limited longevity, limited battery life, and may not monitor all of the desired parameters. As adhesive sensors may be uncomfortable for the wearer, a large sensor size may be a disadvantage. Further, multiple large sensors may become cumbersome for the wearer. For monitoring multiple biometric quantities, different disparate sensors may be required for each quantity, with each sensor being responsible for establishing and maintaining secure and reliable communications with an external server. Moreover, sensors for biometric quantities may require sourcing from different vendors. As a result, separate network support for the different sensors may be required raising costs and complexity.

SUMMARY

Various embodiments provide methods and devices directed to measuring one or more physical or physiological parameters of a body. An embodiment device may include a patch, a sensor hub coupled to the patch, and at least one detachable sensor pod detachably coupled to the patch. In some embodiments, a plurality of detachable sensor pods may be coupled to the patch. The patch may include a flexible adhesive substrate and a flexible layer integrated with the flexible adhesive substrate. The flexible layer may support the sensor hub and sensor hub wiring coupled to the sensor hub. The patch may further include at least one docking area where the detachable sensor pod may be detachably coupled. In some embodiments, a plurality of docking areas may be provided to accommodate the detachable sensor pod. The docking area, which may be an adhesive docking area, may include a connector coupled to the sensor hub wiring. The sensor hub may include a wireless transceiver, a first energy storage element, and a processor coupled to the wireless transceiver, the sensor hub wiring, and the first energy storage element. The processor may be configured with processor-executable instructions to perform operations that may include establishing a first wireless communication link with a receiver when the sensor hub is within range of the receiver.

In various embodiments, the detachable sensor pod may include a sensor, a second energy storage element, and a transmitter coupled to the sensor and the second energy storage element. The detachable sensor pod may be configured to be coupled to and be powered by the sensor hub through an electrical connection on the patch when the detachable sensor pod is attached to the docking area. The detachable sensor pod may transmit sensor data to the sensor hub via a second wireless communication link established between the detachable sensor pod transmitter and the sensor hub wireless transceiver when the detachable sensor pod is detached from a docking area.

In further embodiments, the sensor hub may further include a first indicator coupled to the processor, and the processor may be configured with processor-executable instructions to perform operations including providing a first indication on the first indicator when the first wireless communication link is established with a receiver. The processor may be configured with processor-executable instructions to perform operations that may further include providing a second indication on the first indicator regarding proper placement of the detachable sensor pod on a body when the detachable sensor pod is detached from a docking area, such as a first version (e.g., green) of the second indication when a placement criterion is satisfied and a second version (e.g., red) of the second indication when the placement criterion is not satisfied.

In further embodiments, the docking area may be disposed on a protrusion of the flexible substrate and the flexible integrated layer, and the protrusion(s) may be configured to enable the integrated sensor array to be affixed to a surface having an irregular contour. In some embodiments, a plurality of protrusions may be provided on the patch as docking areas to accommodate a plurality of sensor pods. The protrusion may be further configured to distribute a force generated by removing the detachable sensor pod from the docking areas in order to resist tearing.

In an embodiment, a processor on the detachable sensor pod may be configured with processor-executable instructions to perform operations such that the second indication regarding proper placement of the detachable sensor pod on a body is determined by comparing signals from the sensor to a threshold value of acceptable sensor signals, and generating the second indication when the sensor signals satisfy the threshold value based on the comparison. In another embodiment, the detachable sensor pod may further include a second indicator and a processor configured with processor-executable instructions to perform operations to provide a third indication via the second indicator regarding proper placement of the detachable sensor pod on a body by determining a current location of the detachable sensor pod with respect to the body, comparing the current location of the detachable sensor pod with respect to the body to a proper placement location for the detachable sensor pod, and providing the third indication via the second indicator based on whether the current location of the detachable sensor pod compares favorably to the proper placement location for the detachable sensor pod.

An embodiment method of measuring a physical or physiological parameter using an integrated adhesive sensor array including a sensor hub and a detachable sensor pod may include establishing a first communication link between the sensor hub and a wireless receiver, attaching the integrated adhesive sensor array to a body, establishing a second communication link between the detachable sensor pod and the sensor hub, sensing a physical or physiological parameter by the detachable sensor pod, and transmitting sensor data of the physical or physiological parameter from the detachable sensor pod to the sensor hub via the second communication link. An embodiment method may further include transmitting the sensor data from the sensor hub to the receiver via the first communication link. An embodiment method may further include generating a first indication indicating establishment of the first wireless connection between the sensor hub and the wireless receiver. In an embodiment, the second communication link may be a wired communication link when the detachable sensor pod is attached to the integrated adhesive sensor array, or a wireless communication link established between the detachable sensor pod and the sensor hub in response to the detachable sensor pod being removed from the integrated adhesive sensor array.

A further embodiment method may include determining whether a position of the detachable sensor pod on the body is proper for measuring the physical or physiological parameter when the detachable sensor pod is removed from the integrated adhesive sensor array, and generating a second indication indicating whether the position of the detachable sensor pod on the body is proper. In an embodiment method, determining whether a position of the detachable sensor pod on the body is proper for measuring the physical or physiological parameter may include comparing signals from a sensor on the detachable sensor pod to a threshold value of acceptable sensor signals and determining that the position is proper in response to the sensor signals satisfying the threshold value based on the comparison. In an embodiment method, determining whether a position of the detachable sensor pod on the body is proper for measuring the physical or physiological parameter may include determining a current location of the detachable sensor pod with respect to the body, comparing the current location of the detachable sensor pod with respect to the body to a proper placement location for the detachable sensor pod, and determining that the position is proper in response to the current location of the detachable sensor pod comparing favorably to the proper placement location for the detachable sensor pod.

In various embodiments, the first indication, the second indication and the third indication may be one or more of a color display indication, an audible indication, and an alpha-numeric display indication.

Further embodiments include an apparatus for measuring a physical or physiological parameter having means for performing functions of the methods described above.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Figure 1A:
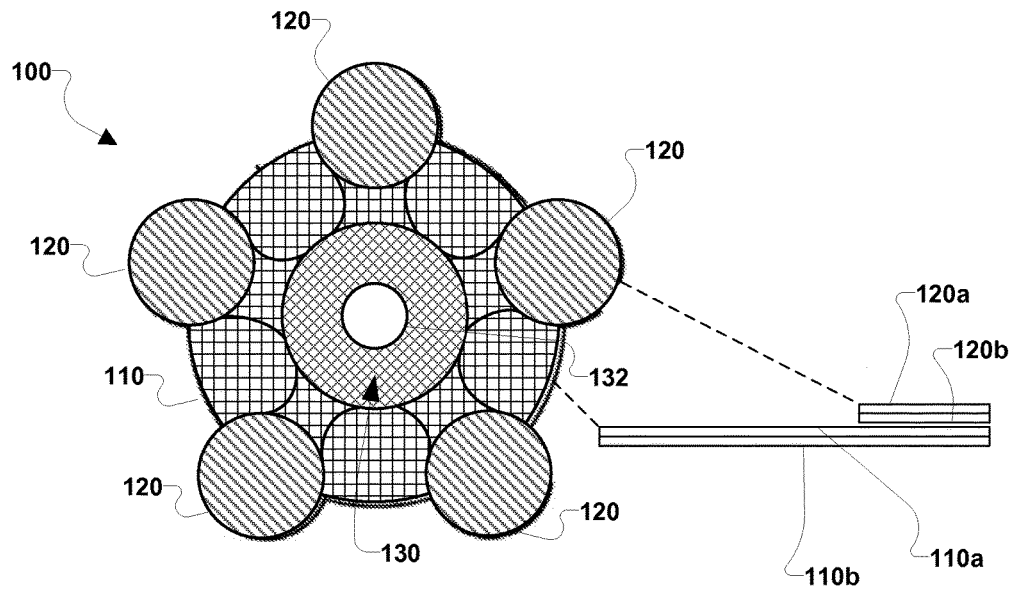
FIG. 1A is a block diagram illustrating an embodiment integrated adhesive sensor array including a central hub and removable sensor nodes.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The terms "device," "computing device," "mobile computing device," as used herein, may refer to any one or all of cellular telephones, smartphones, personal or mobile multi-media players, personal data assistants (PDA's), laptop computers, desktop computers, tablet computers, smart books, palm-top computers, wireless electronic mail receivers, multimedia Internet enabled cellular telephones, televisions, smart TVs, smart TV set-top buddy boxes, integrated smart TVs, streaming media players, smart cable boxes, set-top boxes, digital video recorders (DVR), digital media players, and similar personal electronic devices which include a programmable processor.

The term "access point" as used herein refers to any of network wireless access points, wireless routers, wireless access point repeaters, wireless access point range extenders, bridges, combinations of these device or other devices, which may provide access for a client device to a network operating according to a wireless protocol, such as a WiFi protocol (e.g. under various versions of the 802.11 protocol) or other protocol. Access points are described herein as being wireless, and providing wireless access to a local area network (LAN), a wireless LAN (WLAN), such as a home or private local area network. However, the access points may further have the ability to support wired connections and may be coupled through a wired connection to a service provider, for providing further access to private networks, a public network such as the Internet, or a combination of public and private networks, including medical service provider networks and other related networks.

As used herein, the term "sensor" refers to a device that senses or measures one or more detectable physical phenomena or quantities and generates a signal indicative of a measurement or sensed state, condition or quantity. The signals generated by a sensor may be processed to measure the one or more detectable physical quantities based on a correlation between the signal and the underlying physical quantity. Non-limiting examples of sensors include temperature sensors, pulse sensors, electric field sensors (e.g., electroencephalograph sensors), moisture sensors, liquid flow sensors, magnetic sensors, piezoelectric sensors, pressure sensors, optical sensors, chemical sensors (e.g., blood glucose sensors), and other bio-medical sensors.

As used herein, the term "energy harvesting" refers to mechanisms that convert energy from a variety of energy sources into a form that can be used to power an electrical circuit, such as to power sensor operations. Non-limiting examples of energy sources that may be utilized by energy harvesting elements include patient movements, heat (e.g., the difference in temperature between the patient's skin and air), ambient light (e.g., via a photocell). As described below, Energy generated by an energy harvesting device may be used to power sensor circuits and other sensor components, such as transmitters or transceivers for transmitting information to and receiving information from a monitoring device, or other device that is associated with the sensor.

The various embodiments overcome the drawbacks of proposed wireless adhesive biomedical sensors by providing an integrated adhesive sensor array having a central hub with one or more removable (e.g., peel off or otherwise detachable) sensor nodes or pods attached to the main adhesive sensor patch. The detachable sensor pods may be configured to sense quantities in their original "docked" position on the main adhesive sensor base with the sensor hub unit, communicating with the sensor hub through a wired electrical connection to the sensor hub. One or more of the detachable sensor pods may also be removed and placed in specific locations on a body, such as the body of a human or animal patient, associated with the measured physical quantities (e.g., temperature, pulse rate, B/P, electrical fields, etc.). By placing the detachable sensor pods in specific locations on a body, improved or enhanced measurements of the physical parameters of the body, such as a patient's physical or physiological quantities may be obtained. In various embodiments, some or all of the detachable sensor pods may be configured to be adaptable for measuring different quantities, or the detachable sensor pods may be configured to measure specific physical parameters or quantities.

As used herein, the term "sensor hub" refers to a portion of the integrated adhesive sensor array that receives information from (and optionally transmits information to) detachable sensor pods from the array and may serve as a communication relay to receiver devices or an access point. The sensor hub may communicate with a receiver or access point by wired or wireless communication links transfer information including sensor data obtained from detachable sensor pods. A sensor hub may also receive information from the receiver. The sensor hub may also function as a sensor. As used herein, the term "detachable sensor pod" refers to a sensor unit that may be detachably coupled to the integrated adhesive sensor array. A detachable sensor pod may be configured to sense one or more quantities and communicate information associated with the sensed quantity or quantities to a sensor hub through a wired or wireless connection.

A receiver that receives data from the sensor hub may be a mobile computing device, an access point, or other computing device configured with suitable wireless communication circuitry.

In the various embodiments, the detachable sensor pods may establish a wireless communication link with the sensor hub when removed from the integrated adhesive sensor array. The detachable sensor pods may be configured to communicate sensor data to the sensor hub via a wired connection while attached to the main patch that includes the sensor hub, and via a wireless link when detached from the main patch and placed on the body.

The sensor hub may provide an indication through an indicator, such as a light emitting diode (LED) or other visual indicator, or an audible indicator. Such a display or indication state of the sensor hub may be used provide a confirmation that the sensor hub is successfully paired with a receiver and/or is properly positioned on and attached to the body to obtain reliable sensor readings. Indication states of the sensor hub indicator, possibly together with the detachable sensor pod indicators, may also provide confirmation that the sensor hub is receiving sensor data from a peeled-off, removed or detached, and repositioned detachable sensor pod.

In various embodiments, the detachable sensor pods may also include a status indicator, such as an LED or color changing element. Such a status indicator may provide indications that enable a user to configure and place detachable sensor pods, such as to indicate proper placement of the detachable sensor pods on a body. For example, if a particular detachable sensor pod is configured for measuring a patient's heart beat, removal and placement of the detachable sensor pod in a particularly optimum position for measuring heart beat may be confirmed by way of the sensor hub indicator. For example, a heartbeat detachable sensor pod may illuminate an LED or change color when heart beats are being detected. In some embodiments, a detachable sensor pod indicator may provide further feedback and confirmation to a user regarding placement of the detachable sensor pod.

In an embodiment, a main sensor unit (also referred to herein as the main patch) may be initially configured with detachable sensor pods in the docked position in which the detachable sensor pods are attached to the main patch of the integrated adhesive sensor array. The detachable sensor pods may be configured to be removed, peeled off, or detached from the main sensor unit rather than the skin of a body, such as a patient or wearer, or other delicate surface. By configuring detachable sensor pods to be peeled off or detached from the main sensor unit, potential discomfort or skin or surface tearing may be avoided. Tearing of the patch itself or components thereof may also be avoided. The main sensor unit or patch may include a central communications sensor hub with wired electrical connections to the detachable sensor pods, a power source, a memory and processing capability such as a controller or processor. The sensor hub may communicate wirelessly with the detachable sensor pods when the detachable sensor pods are removed from the main sensor unit. Thus, the integrated sensor assembly and/or sensor hub may include a radio module to communicate data between the sensor hub and either a mobile device or a fixed wireless access point, such as Wi-Fi.

Each of the detachable sensor pods may also include a power source or power storage element (e.g., a battery), a memory, a processor, and a radio module. The radio modules of the detachable sensor pods may be used when the detachable sensor pods are detached to communicate sensor data to the sensor hub radio module.

The main sensor unit or patch may include an adhesive substrate, such as a ring or circular portion of adhesive may be affixed to a bottom surface of the main sensor unit. The adhesive portion may securely attach the main sensor unit to a body, such as the skin of a patient or wearer, or other surface.

The shape of the main sensor unit may include multiple projections that accommodate the detachable sensor pods and allow the main sensor unit to be attached to flat surfaces, or to surfaces having irregular shapes and contours, such as those corresponding to various body parts of the patient or to an object that may ordinarily present attachment difficulties. By "irregular shape" or "contour" reference may be made to surfaces that are generally not flat, which may include curved or irregular surfaces associated with a body or an object. The multiple projections may further minimize wrinkling or binding when the sensor unit is attached.

The main sensor unit may include a grab point such that the main unit may be easily removed. Each of the detachable sensor pods may include a projecting tab or grab point configured for easy removal or detachment of the detachable sensor pod. The detachable sensor pod and the shape of the main sensor unit may be configured to distribute pulling forces throughout the device so as to avoid tearing of the main patch when removing the detachable sensor pods by the projecting tab. In some embodiments, the detachable sensor pod may be re-attached after removal or detachment.

In various embodiments, each of the detachable sensor pods may be configured to measure different physical or physiological parameters, such as temperature, blood pressure, electrophysiology signals (e.g., electrocardiogram (EKG) and electroencephalogram signals), muscle movements, blood oxygenation level, and other physical or physiological parameters. In other embodiments, some or all of the detachable sensor pods may be configured to measure the same physical or physiological parameters. In some instances placement of multiple detachable sensor pods configured for the same measurement quantity (e.g., EKG) in specific locations may improve the quality of the sensor reading. Some or all of the detachable sensor pods may remain docked to the main sensor unit or patch section and the detachable sensor pods may function to provide readings to the sensor hub through wired connections through a contact or connector. The sensor hub may provide a power connection to the detachable sensor pods through the contact or connector.

Some or all of the detachable sensor pods may be detached or peeled away from the main patch and placed on a specific part of the body. When the detachable sensor pods are detached from the main sensor unit or patch and connector, a radio module may be activated along with a local power source or storage element for the detachable sensor pod. The detachable sensor pod may pair with the sensor hub and an indication on either or both of the detachable sensor pod or sensor hub may be provided to confirm successful pairing. A further indication may be provided when the detachable sensor pod is placed in an optimum position on the body. The further indication may also be provide when the detachable sensor pod is placed at least in a position to obtain a sufficient measurement associated with the designated physical or physiological parameter.

As discussed above, wireless communications may be activated between a detachable sensor pod and the sensor hub when a detachable sensor pod is detached from the main sensor unit or patch. In an embodiment, detachable sensor pods may be re-attached to the main sensor unit or patch which may electrically connect them to the sensor hub through an electrically conductive contact or connector. When the detachable sensor pod is electrically connected to the sensor hub through the connector, a wireless communication link to the sensor hub may be discontinued in favor of a low-power wired communication link. In further embodiments, the detachable sensor pods may communicate wirelessly with the sensor hub even when docked on the same adhesive substrate.

A detachable sensor pod may be connected (or reconnected) to the main sensor unit or patch and may be powered by a power supply or power source associated with the sensor hub, which may include recharging a battery within the detachable sensor pod if powered by a rechargeable battery. Alternatively, the detachable sensor pod may be powered by its own power source, such as a battery, an energy harvesting element (e.g., a photocell), or other energy storage device. In some embodiments, one or more of the sensor hub and detachable sensor pods may be powered through an energy harvesting or self charging mechanism.

As mentioned above, an indicator on the sensor hub and/or the detachable sensor pods may display an indication or confirmation of a pairing and placement state of the sensor hub and the detachable sensor pods. The display may be a simple display, such as a two color display. In an embodiment, colors may be formed through an electrochemical reaction mechanism, an electroluminescence mechanism, a plasma display mechanism, an INDIGLO® plasma display mechanism, an LED array, flexible display, or other display mechanism. The display may further be configured to provide an alphanumeric display, or a combination of alphanumeric and color display. The display may further alternatively, or in addition to, provide an audible output, audible indication, or audible "display." The audible indication may include a beep, a buzz, a click, or other audible indication or series of audible indications. The indication may be tactile including a vibration or series of vibrations.

As an example, when the main sensor unit may be paired and activated when the main sensor unit is brought near a mobile computing device or access point configured to act as a receiver of sensor data, in response to which the indicator can change from one color to another. For example the indicator could change from red indicating that no connection has been established to green to indicate that the sensor hub and the mobile communication device are successfully paired. Alternatively, an alphanumeric indication may display a word, code, or message indicating successful pairing or placement.

In some embodiments, the sensor hub and/or detachable sensor pods may not be provided with indicators. Rather, a receiver device, such as a smartphone, may be configured with an application that interfaces with the sensor and presents a display of information on the receiver's display regarding a quality of the communication link, quality of sensor data being received, an indication of whether a sensor is properly placed on the body, and other indications as described herein. The indications provided by the receiver device may include indications that the sensor hub is paired with the receiver and/or that the sensor hub is paired with the detachable sensor pods. The indications provided by the receiver device may further provide feedback regarding favorable or adequate placement of the sensor and/or the detachable sensor pods. For example, the indications presented on the receiver device display may include different colors or indications when the sensor is placed in a suitable location on a patient's body compared to when it is positioned over an improper or unsuitable location on the body. The indications presented on the receiver device display may include indications that provide feedback for the placement of the detachable sensor pods when the detachable sensor pods are detached from docking stations and placed in specific locations.

The indicator or indicators on the sensor hub and detachable sensor pods may be activated by processors configured to assess the appropriateness of the location on and connection to the body. To accomplish this, the processors may receive information regarding the positioning of the sensor hub or detachable sensor pod with respect to the body, such as signals from a wireless coordinate reference system, or sample signals from sensor(s) to confirm that suitable sensor signals are being received. In embodiments that use information from a body coordinate reference system, the processor in the sensor hub or detachable sensor pod may compare its determined coordinates with respect to the body to a database of coordinates appropriate for placement of the sensor. For example, when the main sensor unit or patch is held over different parts of the body, the indicator may provide an indication, such as a red or green indication, when the position of the sensor unit would result in an incorrect placement to sense the physical or physiological parameters measured by the sensor (i.e., sensor hub or detachable sensor pod). In other embodiments, the processor may sample sensor data as it is applied the body, compare the sensor data to various acceptability thresholds (e.g., magnitude of the sensed physical or physiological parameter, noise level, or sensor data pattern) and provide an acceptable indication, such as a green color or light, when the sensor data satisfies such thresholds, and provide an unacceptable indication, such as a red color or light, when the sensor data does not satisfy such thresholds. This feedback indicator may assist a clinician in the placement of the sensor hub and/or detachable sensor pods. Such indicators may be included on both the sensor hub and the detachable sensor pods, and may function independently regarding each sensor's position on the body.

In an embodiment, an indicator may be configured to provide an audible indication of acceptability or alert when the sensor position is incorrect, the sensor is not detecting physical or physiological parameter(s) or a data connection is not available.

In a further embodiment, the sensor hub may include display configure to present sensor data in a user-readable manner, such as a numerical value for the measured physical or physiological parameter (e.g. temperature or heart rate) or a message indicating that an action is required of the clinician. For example, a displayed message may indicate that the clinician should replace the sensor hub (e.g., the battery is low or a component is malfunctioning), administer a medication, or referring to a medical application, such as may be executing on a mobile device of the user, for further instructions.

An embodiment of an integrated adhesive sensor array 100 is illustrated in FIG. 1A. In the illustrated embodiment, the integrated adhesive sensor array 100 may include a main sensor unit or patch 110 on which are positioned in sensor hub 130 and the plurality of sensor hubs 120. The main sensor unit or patch 110 may have a foundation or substrate layer 110a and an adhesive layer 110b configured to adhere the main sensor unit or patch 110 to a body. The substrate layer 110a may be constructed of a material having a degree of flexibility depending on the application. The degree of flexibility may balance ease of application of the main sensor unit or patch 110 to curved body contours, while maintaining the ability to provide structural support. The main body may accommodate a plurality of detachable sensor pods 120, which may also have a degree of flexibility so as to be capable of being easily removed from the main sensor unit or patch 110 and placed on and removed from curved contours of a body. The relative flexibilities of the main sensor unit or patch 110 and the detachable sensor pods 120 may be configured such that when the main sensor unit or patch 110 is flexed to be applied to curved body contours, or to objects, the detachable sensor pods 120 may flex in a corresponding manner.

The adhesive layer 110b of the main sensor unit or patch 110 may be constructed as a separate layer that includes adhesive or as an adhesive layer applied to the substrate layer 110a.

The detachable sensor pods 120 may also have a substrate layer 120a on which an adhesive or an adhesive layer 120b may be constructed. The adhesive layer 120b on the substrate layer 120a of the detachable sensor pods 120 may be attachable to a docking area on the main sensor unit or patch 110 that may or may not also have adhesive. Alternatively, the detachable sensor pods 120 may have a film (not shown) covering and protecting the adhesive layer 120b until the detachable sensor pod 120 is attached. Such a protective film may be attachable to an adhesive that is present in the docking area. Alternatively, the film itself may have an adhesive that attaches to the docking area of the main sensor unit or patch 110. When the film is removed, the adhesive on the sensor pods 120 may be used to attach to the surface of the body, such as the skin of the patient.

Figure 1B:
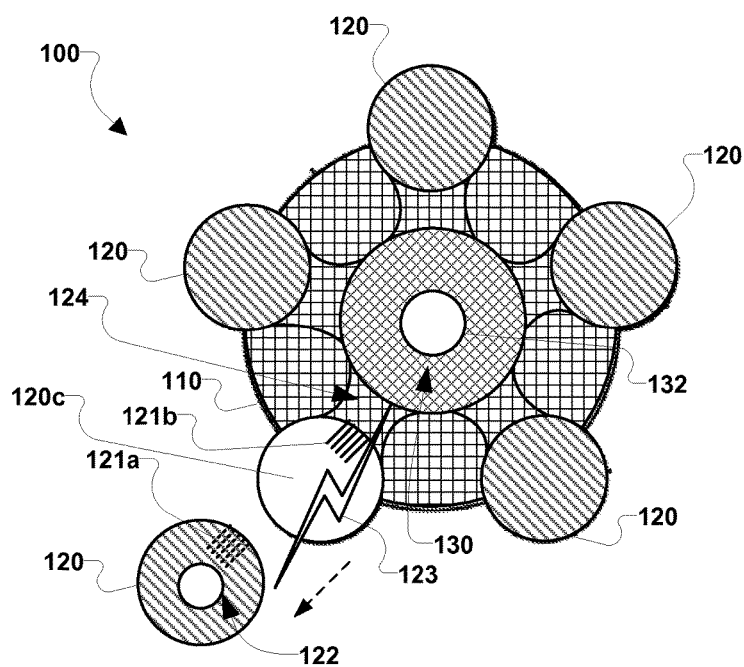
FIG. 1B is a diagram illustrating an embodiment integrated adhesive sensor array including a central hub and removable sensor nodes and a removed node.

As described above, each of the detachable sensor pods 120 may be configured to be removed from the main sensor unit or patch 110 and applied to another portion of the body. FIG. 1B illustrates one of the detachable sensor pods 120 removed from the main sensor unit or patch 110, with a wireless communication link 123 established to the sensor hub 130. The detachable sensor pods 120 may be configured with one or more electrical connectors 121a on the bottom surface of the adhesive layer 120b that interface with the one or more electrical connectors 121b on the top surface of the substrate layer 110a when the detachable sensor pod 120 is attached to a docking area 120c on the main sensor unit or patch 110. Such electrical connectors 121a may be individual contact strips, pads or pins. The electrical connectors 121a may be flexible or at least may be configured to be compatible with flexion during removal and application of the detachable sensor pod 120 from a docking area 120c of the main sensor unit or patch 110. The docking area 120c for the detachable sensor pod 120 may be configured with corresponding electrical connectors 121b that mate with the detachable sensor pod electrical connectors 121a for providing direct electrical contact to the sensor hub 130. Such electrical connectors may provide power to sensors within the detachable sensor pod 120 as well as a wired communication link for transmitting sensor data from the detachable sensor pod to the sensor hub 130.

When the detachable sensor pod 120 is coupled to the docking area 120c on the main sensor unit or patch 110, sensor data from an integrated sensor may be communicated to the sensor hub 130 via the electrical connectors 121a, 121b. When the detachable sensor pod 120 is removed from the docking area 120c of the main sensor unit or patch 110, a wireless communication link 123 may be established between a radio module within the detachable sensor pod 120 and a radio module of the sensor hub 130.

The docking area 120c of the main sensor unit or patch 110 may be coupled to the sensor hub 130, or to an area accommodating the sensor hub 130 with an arm 124. The arm 124 may be a reinforced area that extends from a central area of the main sensor unit or patch 110 to the docking area 120c of all the detachable sensor pods 120. The arm 124 may provide strength to the main sensor unit or patch 110 and the sensor assembly including the detachable sensor pods 120. Reinforcement provided by the arm 124 may be useful during placement of the main sensor unit or patch, detachment of the detachable sensor pods 120, manipulation of the detachable sensor pods 120 or other movements of the sensor, such as body movements when the sensor is in place.

As illustrated in FIGS. 1A and 1B, the sensor hub 130 may include an indicator 132, such as a light emitting diode (LED) or color changing display material that is configured to provide an indication of operation of the sensor assembly, such as communication pairing with the detachable sensor pod 120, correct positioning on a body, and/or successful reception of appropriate physical or physiological sensor data. Similarly, the detachable sensor pods 120 may also be provided with an indicator 122 (e.g., an LED or color changing display) for providing various indications regarding the status of the detachable sensor pod 120, including the connection status, the pairing status, the sensing status or proper location on the body.

In some embodiments, the main sensor unit or patch 110 may be used in an application not associated with placement of the main sensor unit or patch 110 including the sensor hub 130 and/or detachable sensor pods 120 on a body or object. Instead, the main sensor unit 110, or one or more of the detachable sensor pods 120 and the sensor hub 130 may be used in a proximity application where the sensor is placed not on a body but near a quantity to be sensed. The main sensor unit 110, or one or more of the detachable sensor pods 120 and the sensor hub may be used in an application where the one or more of the components, such as the detachable sensor pods 120, are placed directly into a quantity requiring sensing. Once example may include periodically monitoring of a patient-related quantity that does not involve placement of the sensor on a body or object. For example, periodic monitoring may be conducted by removing or "peeling off" one of the detachable sensor pods 120 and placing the detached sensor pod 120 into a urine stream or into another environment where sensing of one or more quantities may take place. The detachable sensor pod 120 may then report the values to the sensor hub 130 which may store the sensor values and communicated to a receiver device. The detachable sensor pod 120 may then be disposed of. When the patient is required to take another reading at a later time, another one of the detachable sensor pods 120 may be peeled off and used for the next monitoring or sensing activity.

Further applications may include "throw" applications, where the main sensor unit or patch 110, or a detached sensor pod 120 is thrown into a location, to detect aspects of the location such as temperature, light, the presence of a gas, or other aspect or quantity. The above examples are intended to be non-exhaustive and non-limiting, as many other applications of the various embodiments are possible.

Figure 2A:
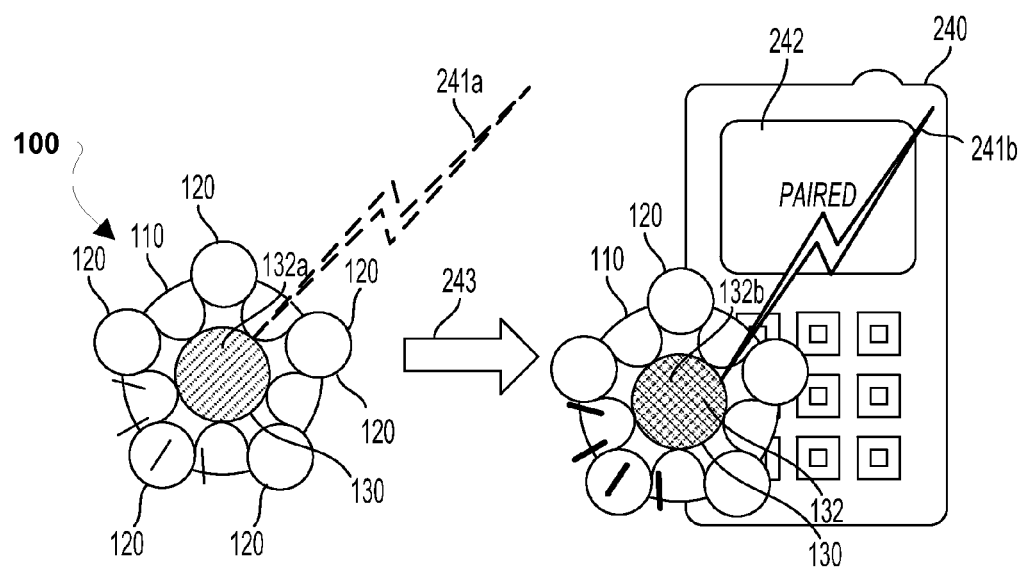
FIG. 2A is a diagram illustrating an embodiment sensor pairing with a mobile computing device and providing an indication.
Figure 2B:
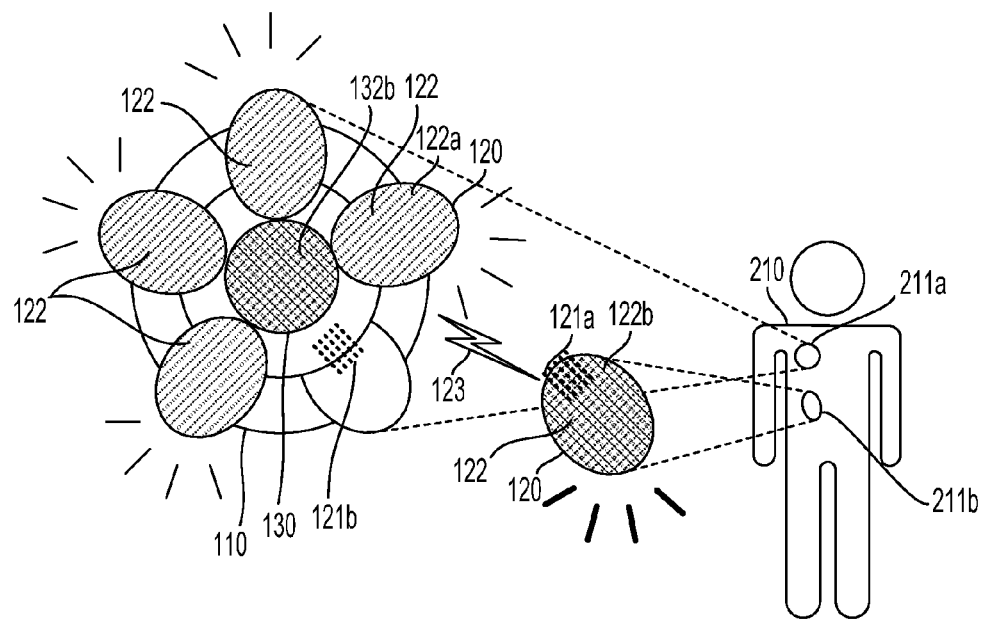
FIG. 2B is a diagram illustrating an embodiment removable sensor removed from main sensor unit or patch, paired with a hub, positioned on a body and providing an indication.

In an embodiment illustrated in FIGS. 2A and 2B, the sensor hub indicator 132 and/or detachable sensor pod indicator 122 may be formed on a top surface of the sensor hub and detachable sensor pod, respectively. Thus, the entire top surface of the sensor hub and/or detachable sensor pods may be an indicator that changes color to indicate status or state as described herein.

FIG. 2A also illustrates an example of establishing a communication link between an integrated adhesive sensor array 100 and a mobile computing device 240 for communicating sensor data. In use, the main sensor unit or patch 110 with detachable sensor pods 120 in place and a sensor hub 130 may be activated, or at least activated for the purposes of establishing the communication link ("pairing"), by activating or energizing at least the sensor hub 130. When the sensor hub 130 is activated, a radio signal 241a may be transmitted from the sensor hub 130. The radio signal 241a may be in the form of a pairing request packet according to a communication protocol, such as a probe-like signal, a connection request signal, a Bluetooth advertising packet, or other pairing-related signal.

When the integrated adhesive sensor array 100 and a mobile computing device 240 are not within communication range, the radio signal 241a may not be received and pairing may not occur. Before pairing has occurred, the indicator 132 on the sensor hub may display a first color or indication 132a, indicating that a communication link is not yet been established.

When the sensor is moved (243) into communication range of the mobile computing device 240, the radio signal 241b may be received by the mobile computing device 204 and pairing may take place. When pairing takes place between the sensor hub 120 and the mobile computing device 240, a display 242 of the mobile computing device 240 may provide an indication of the pairing, for example, by displaying a "Paired" message. Also, the indicator 132 of the sensor hub 130 may provide an indication 132b to indicate that pairing has occurred, such as a changing color (as illustrated by the change in hashing in FIG. 2A).

In a further example illustrated in FIG. 2B, the detachable sensor pods 120 may also be configured with indicators 122 to provide an indication of a status of communication pairing between the detachable sensor pods 120 and the sensor hub 130. The main sensor unit or patch 110, along with the detachable sensor pods 120 and the sensor hub 130 may be placed on a patient 210 at a placement location 211a. The placement location 211a may be in an area that is suitable for the placement of the main sensor unit or patch 110 based on various medical and physical or physiological considerations. For example, the placement location 211a may a location suitable for measuring a particular physical or physiological or biomedical parameter (e.g., pulse, blood pressure, EKG electrical fields, etc.). The placement of the main sensor unit or patch 110 may also depend on other considerations such as proximity to a receiver device (e.g., a mobile computing device 240) or system with which the integrated adhesive sensor array 100 may communicate sensor data.

When the detachable sensor pods 120 are in place on the main sensor unit or patch 110 and electrically coupled to the sensor hub 130, an indicator 122 may provide an indication 122a of the status of the detachable sensor pods 120. The status could be indicated as, for example, connected to the sensor hub and operational. The indication could be a color-coded indication that specifically indicates a specific status based on the color. Alternatively, the indication could be a numerical or alphanumerical indication that indicates a status code, a sensor reading value, an alphanumeric indication of the sensor status or other indication.

When a detachable sensor pod 120 is removed from the integrated adhesive sensor array 100 and the electrical contact between the electrical connectors 121a and 121b is interrupted, a radio signal 123 may be transmitted from a radio module or transmitter (or transceiver) on the detachable sensor pod 120. The radio signal 123 may be configured to establish a wireless communication link with the sensor hub 130, which may be equipped with its own radio module or receiver for receiving the signal 123. The sensor hub 130 may radio module may be a transceiver that is configured to also transmit data or commands to the detachable sensor pod 120, provided the detachable sensor pod 120 is equipped with a receiver (or transceiver). When the detachable sensor pod 120 is removed and a wireless communication link is established with the sensor hub 130, the detachable sensor pod indicator 122 may provide a different indication 122b. The indication 122b (such as a picture color) may indicate that the sensor has paired with the sensor hub, other indications.

A removed detachable sensor pod 120 may be placed in a placement location 211b of the patient, such as an area where a specific physical or physiological parameter associated with the sensor may be measured or sensed. Since the suitability of the placement location 211b may particular physical or physiological parameter being measured by the detachable sensor pod 120, the indication 122b may also or alternatively be used to provide feedback to the clinician regarding the proper placement of the detachable sensor pod 120. In various embodiments, the detachable sensor pod indication 122b may be provided together with the sensor hub indication 132b on the sensor hub 130 to provide feedback regarding the placement of the detachable sensor pod 120.

Figure 2C:
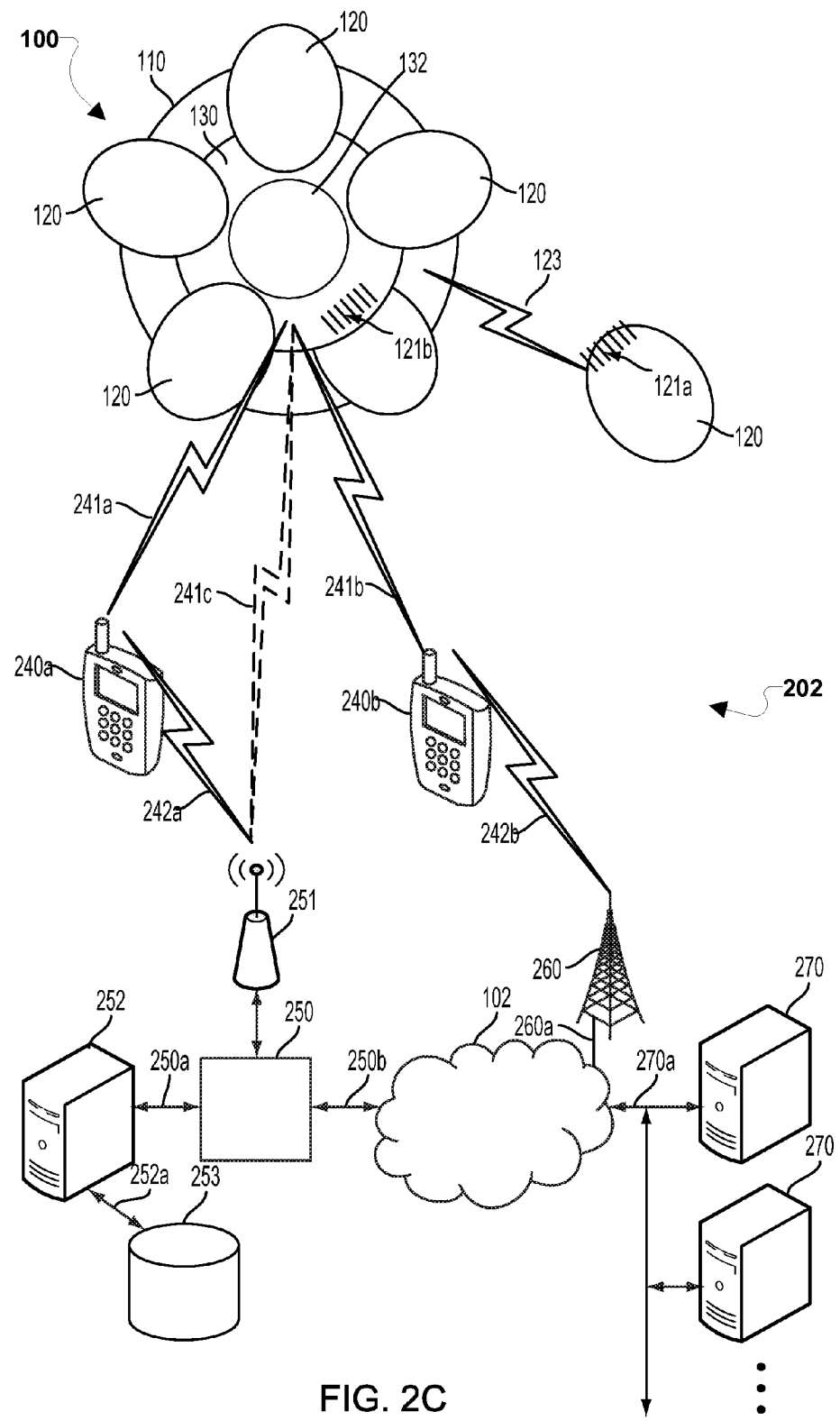
FIG. 2C is a communication system diagram illustrating an embodiment system suitable for implementing a sensor with removable sensor nodes, including mobile computing devices, a personal network, a public network (e.g., Internet), and a private network (e.g., medical network).

When data communications are established between the detachable sensor pods 120 and the sensor hub 130 and between the sensor hub 130 and a mobile communication device 240, the integrated adhesive sensor array 100 may form a part of a medical or physical or physiological monitoring system. An example embodiment system or communication system 202 in which the integrated adhesive sensor array 100 may be used is illustrated in FIG. 2C. As discussed above, an integrated adhesive sensor array 100, including a sensor main body 110, a plurality of detachable sensor pods 120, a sensor hub 130, may be attached to a body, such as a patient or wearer. One or more of the detachable sensor pods 120 may be removed from the sensor main unit or patch 110 and placed in various locations on the body, such as the body of the patient or wearer. In various embodiments, the detachable sensor pods 120 may communicate with the sensor hub 130 through a wireless communication link 123 or a wired communication link via the electrical connectors 121a and 121b as described above.

The sensor hub 130 may be paired with a mobile communication device 240a through a wireless communication link 241a. The mobile communication device 240a may be in communication with a receiver 250 through a wireless communication link 242a. The wireless communication link 242a may be established through an antenna 251 coupled to the receiver 250, which may be a wireless access point or other receiving device. The receiver 250 may further be coupled to a computing device 252 through a connection 250a and to a network 102 through another data connection 250b. The computing device 252 may be coupled to a storage device 253 through a data connection 252a. The storage device 253 may be an external or internal storage device, such as a mass storage device or memory device. The storage device 253 may be used to store accumulated information, such as data readings from the sensor, including the detachable sensor pods 120. The storage device 253 may further store other information, such as patient or wearer information, medical condition and/or procedure information, or other information. In an alternative embodiment, the sensor hub 130 may communicate directly with the receiver 150 through a wireless communication link 241c to the antenna 151 of the receiver 250.

When a connection to a network 102 is present, the computing device 252 may connect, for example, with a medical system through servers 270. The medical system may use it sensor data received by the communication system 202 from the integrated adhesive sensor array 100 to enable remote monitoring of the body by allowing readings from the sensors to be transmitted in real-time. The communication system 202 may further enable a caregiver to monitor patient data and provide a remote diagnosis. The patient and medical information stored in the storage device 253 may be forwarded to a medical system for collection and storage, such as for record keeping and analysis. The sensor readings may be used to automatically trigger alerts in the medical system when certain conditions arise. In such a case the indicators on the sensor hub 130 and the detachable sensor pods 120 may be activated to provide alert indications.

In various embodiments, the sensor may be coupled to a mobile computing device 240b that may provide communications with the medical system servers 270 through a cellular connection to the network 102. The sensor hub 130 may establish a connection 241b with the mobile computing device 240b. The mobile computing device 240b may be coupled to cellular network through a connection 242b to a wireless infrastructure component 260, such as an antenna of a cellular base station. The wireless infrastructure component 260 may be coupled to the network 102 through a connection 260a. The network 102 may be representative of a network or combination of networks that provide communications and data transfer between various network elements or nodes. The network 102 may include a public network, private network, or combination of public and private networks. The network 102 may also include a public switched telephone network capable of carrying voice and data traffic. The mobile computing device 240b may connect to the medical system servers 270 to provide readings from the sensors directly to the medical system. The sensor readings may be analyzed, recorded, stored in storage devices (not shown) associated with the servers 270 and/or the medical system.

Figure 3A:
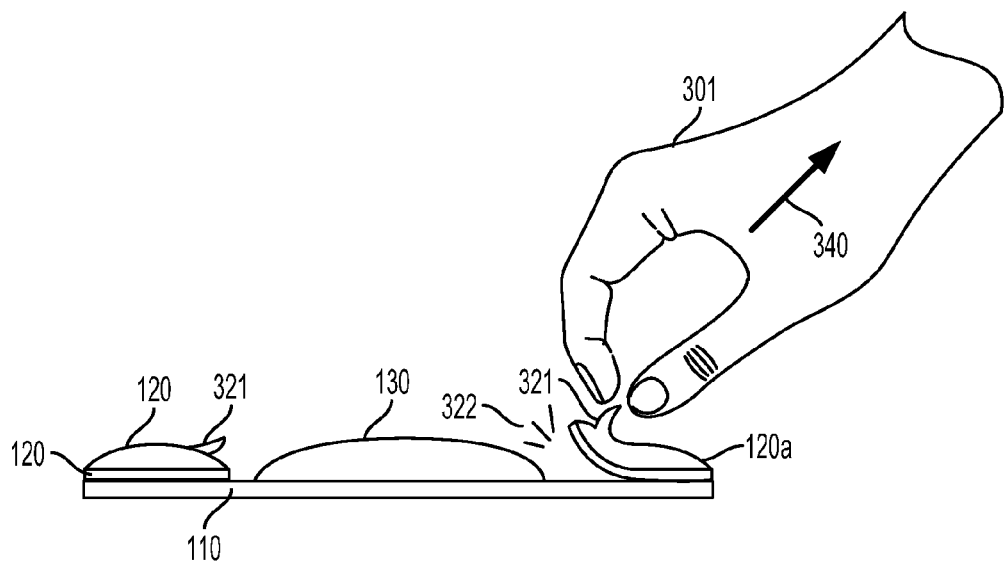
FIG. 3A is a diagram illustrating removal of a removable sensor node from an embodiment sensor main body.

In various embodiments, the integrated adhesive sensor array 100 may be configured to be flexible and resilient so that placement of the main sensor unit or patch 110 and removal (and replacement) of the detachable sensor pods 120 does not damage the sensor. FIG. 3A illustrates an example of how the integrated adhesive sensor array 100 may be configured so that the detachable sensor pods 120 may be removed while reducing the possibility of tearing of the main sensor unit or patch 110, the docking areas for the detachable sensor pods 120 and the detachable sensor pods 120 themselves. The docking area for the detachable sensor pods 120 may be attached to the main sensor unit or patch 110 through arms 334. Tearing may be a concern, particularly when individual detachable sensor pods are detached. To reduce the chance of tearing, the detachable sensor pods 120 may be provided with a pull tab 321. A user 301 may grip the pull tab 321 and apply a removal force 340 to the pull tab 321 to remove the detachable sensor pod 120 from the main sensor unit or patch 110 as illustrated in FIG. 3A. The removal force 340 may be sufficient to overcome the adhesive force supplied by the adhesive that attaches the detachable sensor pod 120 to the main sensor unit or patch 110.

Figure 3B:
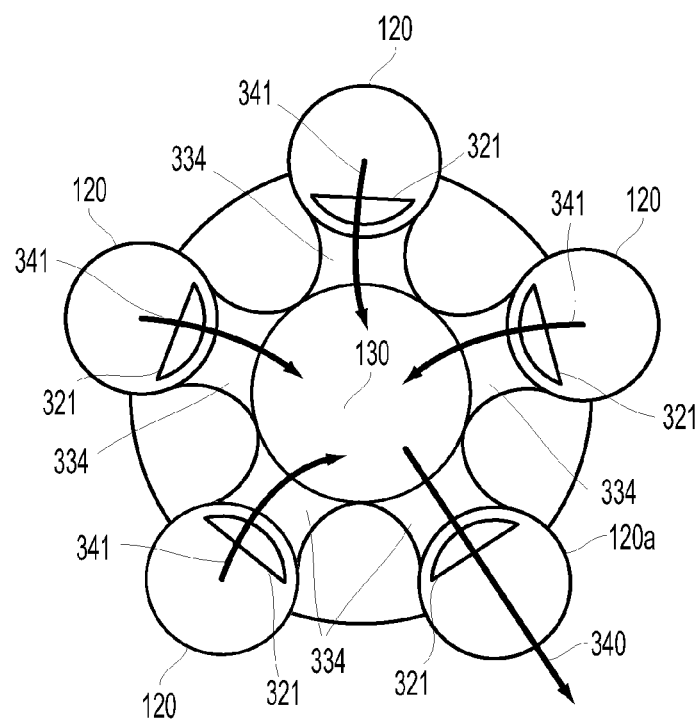
FIG. 3B is a diagram illustrating the force distribution paths of removal forces for removing an embodiment removable sensor node.

In an example illustrated in FIG. 3B, the sensor may be arranged in such a way that the removal force 340 is distributed to prevent tearing. The detachable sensor pods 120 are attached to the main sensor unit or patch 110 through the arms 334. The arms 334 may serve to reinforce the docking area for the detachable sensor pods 120 and may distribute the force 340. For example, when the detachable sensor pod 120a is removed by applying the removal force 340, the removal force 340 is distributed to all of the sensor arms 334 as illustrated by the arrows 341. Distribution of the removal force 340 in this manner prevents a local concentration of the removal force 340 in the area of the detachable sensor pod 120a to prevent tearing in the area during removal. Torsional or twisting forces may also be developed during the removal of the detachable sensor pod 120a. By providing the arms 334, the torsional forces may also be distributed depending on the construction of the arms 334. For example, the arms 334 may be constructed to have a degree of torsional rigidity that resist localized tearing of the sensor body or components of the sensor body.

Figure 3C:
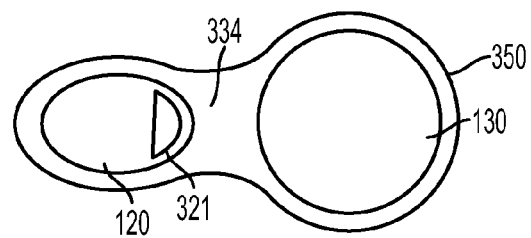
FIG. 3C-FIG. 3G are diagrams illustrating alternative embodiments of removable node sensors.
Figure 3D:
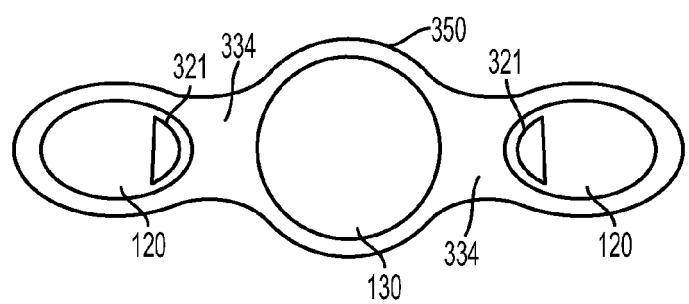
Figure 3E:
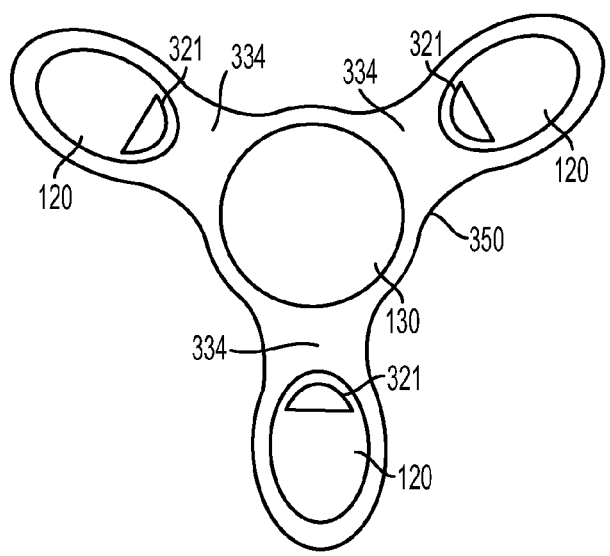
Figure 3F:
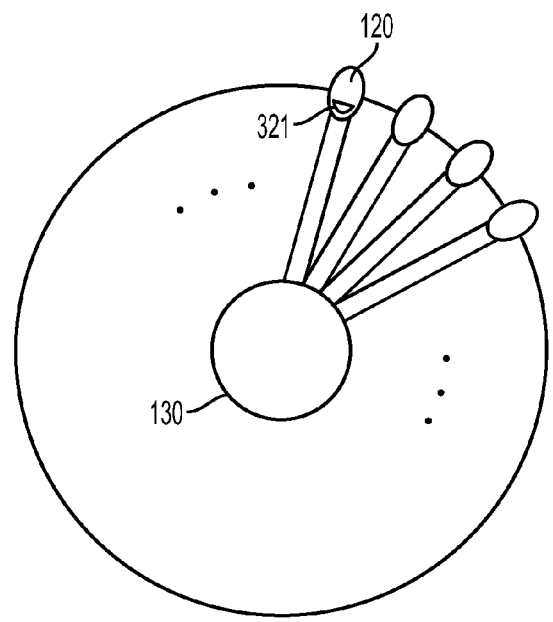

While the examples illustrated in FIGS. 3A-3B include five detachable sensor pods 120, the integrated adhesive sensor array 100 may be configured to include any number of detachable sensor pods 120, from a single pod 120 as illustrated in FIG. 3C, to two detachable sensor pods 120 illustrated in FIG. 3D, three detachable sensor pods 120 illustrated in FIG. 3E. As shown in FIG. 3F, the number of detachable sensor pods 120 may be limited only by the available space on the sensor main body 110 and the size of the detachable sensor pods 120. In some embodiments, the sensor may be equipped with a large number of detachable sensor pods 120, some or all of which may be used in-place forming a measurement array that may provide improved accuracy in the measurement of the physical or physical or physiological parameter.

Figure 3G:
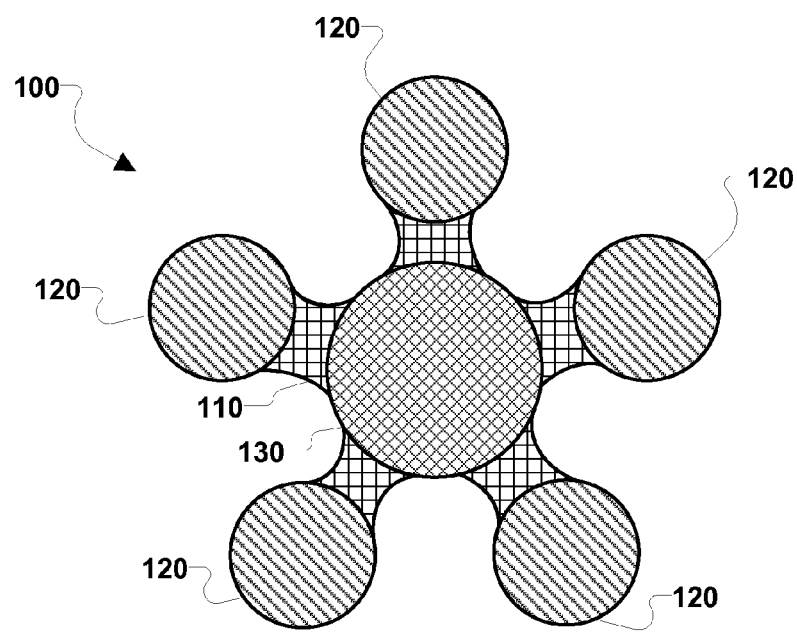

FIG. 3G illustrates an embodiment integrated adhesive sensor array 100 in which the main unit or patch 110 has a star shape with the five detachable sensor pods 120 positioned on the points of the star. This configuration may be advantageous as the star shape enables the integrated adhesive sensor array 100 to better adhere to rounded parts of a patient's body without buckling.

Figure 4A:
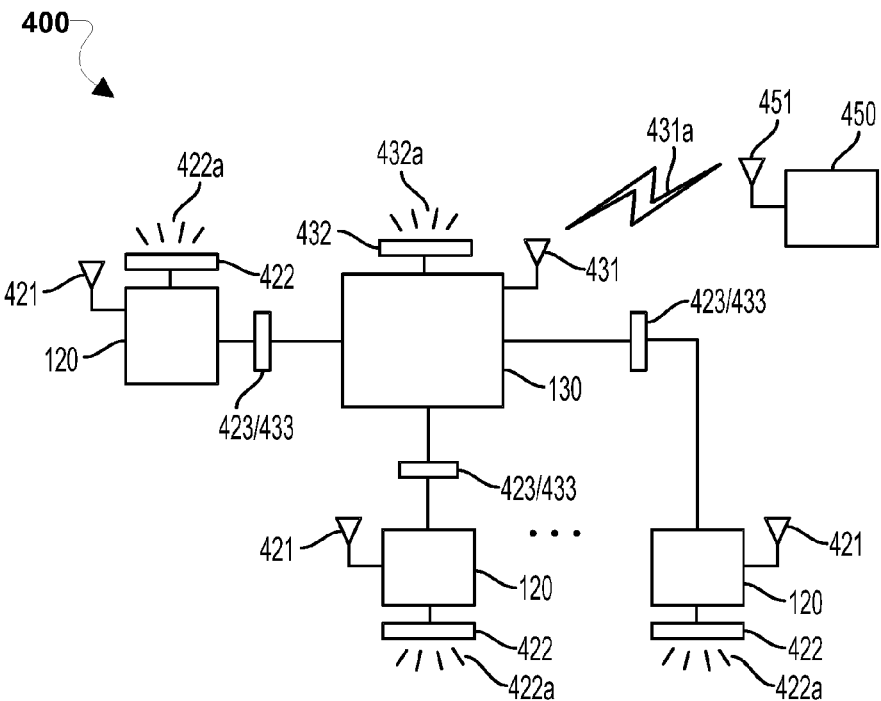
FIG. 4A is a component block diagram illustrating example wireless and wired interconnections of a sensor with removable sensor nodes and a receiver for a sense-in-place configuration.

A components block diagram of an embodiment system 400 of an integrated adhesive sensor array and receiver is shown in FIG. 4A. As in other examples, an integrated adhesive sensor array may include one or more sensor pods 120 and a sensor hub 130.

Each of the detachable sensor pods 120 may include an antenna 421, an indicator 422 for providing an indication 422a, and a connector 423. The indicator 422 may be a visual indicator such as a display. The detachable sensor pod indicator 422 may be an audible indicator such as a piezoelectric element. The detachable sensor pod indicator 422 may be a combination of an audible indicator and visual display.

The sensor hub 130 may include an antenna 431, an indicator 432 for providing an indication 432a, and a connector 433 that may connect the sensor hub to the connector 423 of the detachable sensor pod 120. The sensor hub indicator 432 may be a visual indicator such as a display. The sensor hub indicator 432 may be an audible indicator such as a piezoelectric element. The sensor hub indicator 432 may be a combination of an audible indicator and visual display. The detachable sensor pod connector 423 and the sensor hub connector 433 may be in the form of electrical connectors between the detachable sensor pod 120 and the sensor hub 130, such as through contacts as described above and illustrated in FIG. 1B. The detachable sensor pod connector 423 and the sensor hub connector 433 may also include any of a wide variety of connector supporting structures (not shown) for housing and facilitating electrical connections. The electrical connections between the detachable sensor pod 120 and the sensor hub 130 may be connections that provide power to the detachable sensor pod 120 (e.g., from the sensor hub 130), and provide signal and data connections.

When the integrated adhesive sensor array is within range of a receiver 450, a wireless communication link 431a may be established between the sensor hub 130 and the receiver 450 through an antenna 451. The wireless communication link 431a may allow the sensor hub 130 to transfer information to the receiver 450, such as sensor data or readings from one or more of the detachable sensor pods 120. In various embodiments, the sensor hub 130 may transfer accumulated sensor readings when the integrated adhesive sensor array comes within communication range of the receiver, or may begin to transfer real time sensor readings from one or more of the detachable sensor pods 120 when within communication range the sensor hub 130. The sensor readings may be obtained by the sensor hub 130 through the electrical connections provided by the detachable sensor pod connector 423 and the sensor hub connector 433. When a wireless communication link 431a is established with the receiver 450, the indicator 432 may provide the positive indication 432a or a different indication when the sensor hub has successfully paired with the receiver 450. Each of the detachable sensor pod indicators 422 may be configured to provide an indication 422a when they are successfully communicating with the sensor hub 130. An indication 422a may also be provided when the sensor within the detachable sensor pod 120 is sensing an acceptable or adequate level the physical or physical or physiological parameter of interest. The indication 422a may also indicate whether the sensor is sensing an optimum level of the physical or physical or physiological parameter. The optimum level or the adequate level of the physical or physical or physiological parameter for the detachable sensor pod 120 may be based on information stored in the sensor hub 130. The optimum level or the adequate level of the physical or physiological parameter may also be received by the sensor hub 130 from the receiver 450. The receiver 450 may store information regarding adequate or optimum physical or physiological parameter sensor levels, as well as other information useful for monitoring the sensors and evaluating sensor data. The receiver 450 may also obtain information regarding adequate or optimum sensor levels of physical or physiological parameters from a medical system or server associated with a medical system to which the receiver is or is capable of connecting.

Figure 4B:
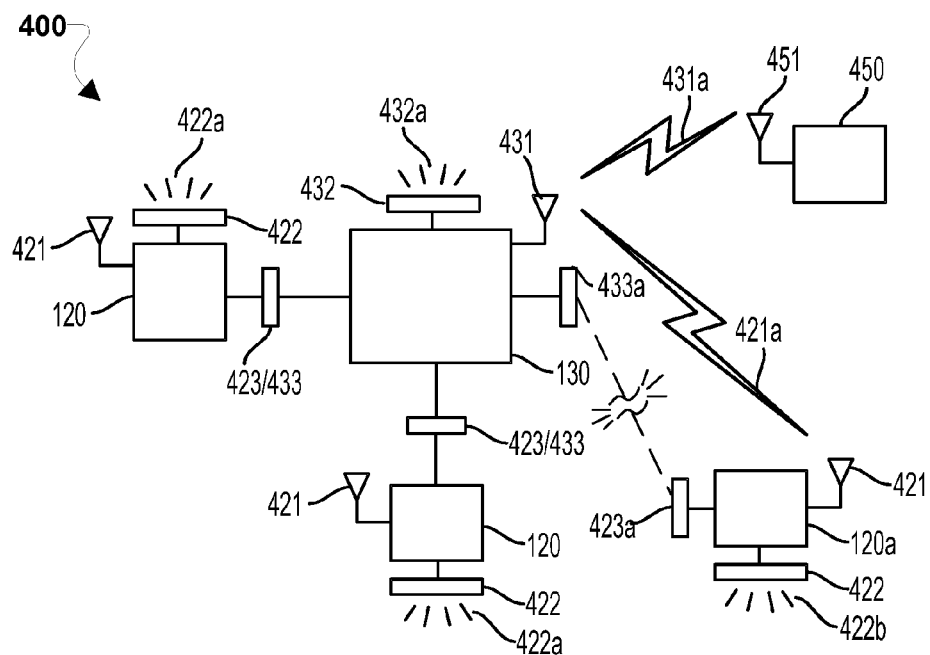
FIG. 4B is a component block diagram illustrating example wireless and wired interconnections of a sensor with removable sensor nodes and a receiver for a configuration in which a removable node is removed.

A component block diagram of the embodiment system 400 of an integrated adhesive sensor array and receiver is shown in FIG. 4B in which one of the detachable sensor pods 120a has been removed from the fish integrated adhesive sensor array. When the detachable sensor pod 120a is removed or peeled away from the sensor hub 130, the electrical contact between the sensor hub 130 and the detachable sensor pod 120a, as provided by the detachable sensor pod connector 423 and the sensor hub connector 433, may be interrupted. This interruption in the electrical connection may cause the detachable sensor pod 120a to begin to use a local power source (such as a battery) and to activate a wireless transmitter or transceiver in the detachable sensor pod 120a. Activation of the transmitter upon interruption in the electrical contact may allow a wireless communication link 421a to be established with the sensor hub 130 through an antenna 431. A display or indication 422 of the detached sensor pod 120a may provide an indication 422b that the detachable sensor pod 120a has established a wireless communication link 421a with the sensor hub 130, as well as other indications. For example, the detachable sensor pod display 422*b* may indicate when the detachable sensor pod 120*a* is properly placed on the body as described above. The indication 422*b* may provide visual feedback to the clinician placing the detachable sensor pod 120*a* on the body, facilitating proper placement.

Figure 4C:
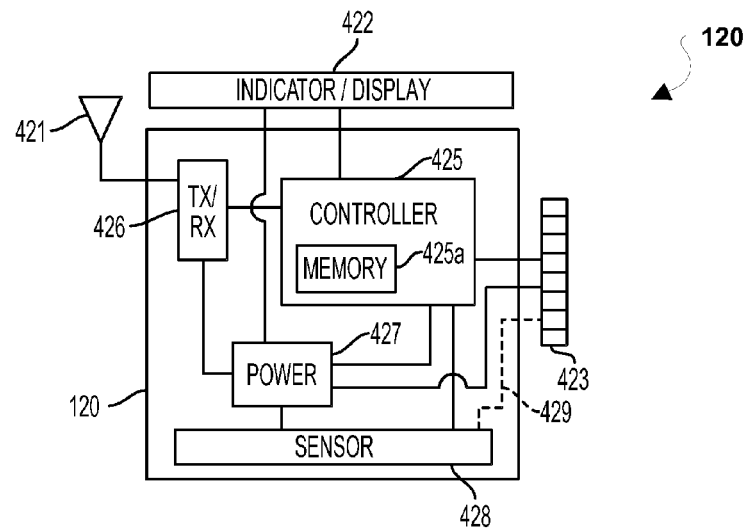
FIG. 4C is a component block diagram of an embodiment sensor node.

A component block diagram of an example embodiment detachable sensor pod 120 is shown in FIG. 4C. As described above, each detachable sensor pod 120 may include an antenna 421, an indicator 422, and an electrical connector 423. In addition, the detachable sensor pod 120 may include a controller 425, which may be a processor that can be configured with processor-executable instructions for controlling the operations of the detachable sensor pod 120 and the interoperation of the detachable sensor pod 120 with other system components, such as the sensor hub 130. The controller 425 may include a memory 425*a* for storing processor-executable instructions for configuring the controller 425 and for storing information, such as sensor data. The controller 425 may be coupled to a transceiver 426, which may operate primarily as a transmitter for transmitting sensor data to the sensor hub 130. In various embodiments, the transceiver 426 may be a transmitter, or may be configured only to transmit. In some embodiments, the transceiver 426 may send data to and receive data from the sensor hub 130.

The detachable sensor pod 120 may further include a power element 427, such as a capacitor, battery, or energy harvesting device (e.g., a photocell), or a combination of an energy harvesting device and a storage element that can be charged or recharged by harvested energy.

The detachable sensor pod 120 may further include a sensor element 428. The sensor element 428 may be configured to sense a single physical or physiological parameter. Alternatively, the sensor element 428 may be configured to sense a variety of biomedical quantities. In another embodiment, the sensor element 428 may be configured as a sensor element and an energy harvesting element. When configured as an energy harvesting element, the sensor element 428 may provide power that is stored in the power element 427. Alternatively, the power element 427, when configured for energy harvesting may, have a separate energy harvesting element (not shown) that takes advantage of one or a number of energy harvesting quantities.

When the detachable sensor pod 120 is connected to the sensor hub 130, such as through the electrical connectors 423, sensor data from the sensor element 428 may be provided directly to the sensor hub 130 through a sensor line 429. In this configuration, the detachable sensor pod 120 may act as a remote sensing unit for the sensor hub 130. Readings or sensor data from the sensor element 428 provided to the sensor hub 130 may be forwarded to a receiver over a wireless communication link as previously described. Alternatively, the sensor data from the sensor element 428 may be provided to the controller 425 and optionally stored in the memory 425*a*. The controller 425 may send the sensor data to the sensor hub 130 in a communication to the sensor hub 130.

Because the integrated adhesive sensor array may be equipped with many detachable sensor pods 120, communications between each detachable sensor pod 120 and the sensor hub 130 may be conducted according to a coordinated protocol to avoid communication interference. When the sensor data is provided directly to the sensor hub 130 the sensor hub 130 may manage and coordinate acquisition of the sensor data from the detachable sensor pods 120.

Figure 4D:
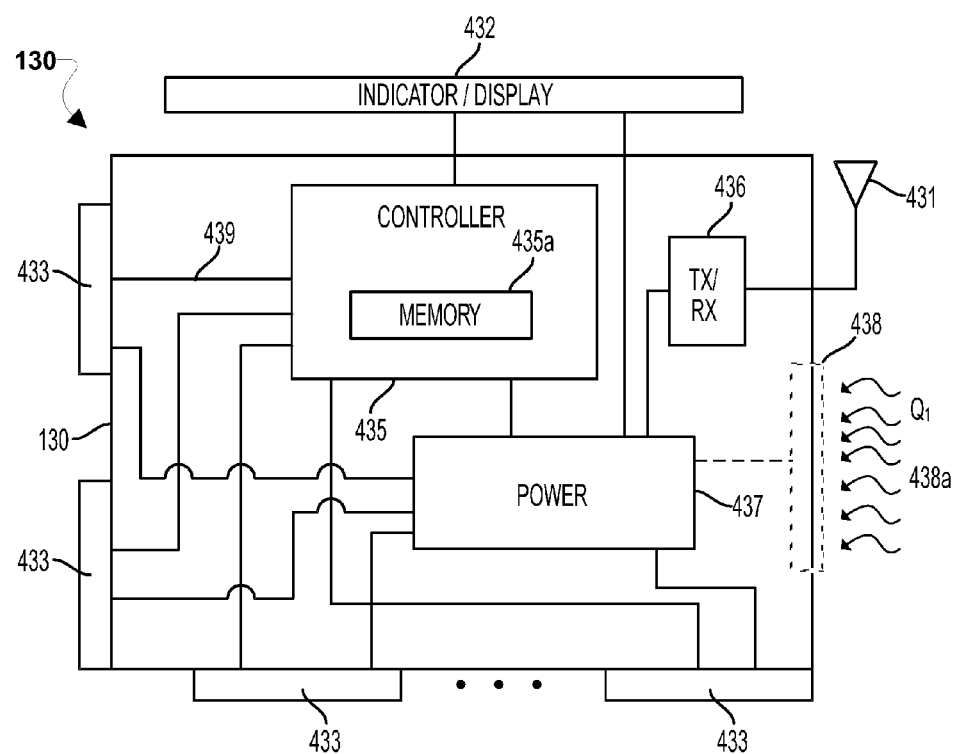
FIG. 4D is a component block diagram of an embodiment sensor hub.

A component block diagram of an embodiment sensor hub 130 is shown in FIG. 4D. The sensor hub 130 may include an antenna 431, an indicator 432, and electrical connectors 433 as previously described. The sensor hub electrical connectors 433 may be configured to connect to the detachable sensor pods 120 through respective detachable sensor pod electrical connectors 423 as described above. The sensor hub electrical connectors 433, when connected to the detachable sensor pod electrical connectors 423, may provide a data connection and a power connection to the detachable sensor pods 120, for example, through wiring associated with the sensor hub 130. For example, the sensor hub electrical connectors 433 may be configured to receive real time sensor signals or output directly from the sensor elements 428 of the detachable sensor pods 120 when connected to the electrical connectors 423 of the detachable sensor pods 120.

In addition, the sensor hub 130 may include a controller 435, which may be a processor that may be configured with processor-executable instructions for controlling the operations of the sensor hub 130 and the interoperation of the sensor hub 130 with other system components, such as the detachable sensor pods 120. The controller 435 include a memory 435*a* for storing processor-executable instructions for operating the controller 435 and for storing information, such as sensor data received from the detachable sensor pods 120. When the detachable sensor pods 120 are electrically connected to the sensor hub 130 through the electrical connectors 433/423, the controller 435 may receive data from the respective controllers 425 over data lines 439.

The transfer of data from the controllers 425 of the detachable sensor pods 120 to the controller 435 of the sensor hub 130 may require coordination so that data transmission collisions do not occur. Such coordination may be accomplished through a networking protocol, multiplexing or other coordination mechanism well known in the communication arts. For example, a network protocol may involve assigning time intervals for each of the controllers 425 to transmit data so that each of the detachable sensor pods 120 transmit the data to the sensor hub 130 at different times. Multiplexing may further be accomplished in hardware (not shown) associated with the sensor hub 130. In a hardware multiplexing scheme, the data from the controllers 425 may be buffered in the controller 435 and accessed in sequence by the controller 435.

The controller 435 may be coupled to a radio module such as a transceiver 436. The transceiver 436 may operate as a receiver for receiving data from the detachable sensor pods 120 when the detachable sensor pods 120 are not electrically connected to the sensor hub 130 through the connectors 433/423. The transceiver 436 may further operate as a transmitter for transmitting the sensor data to the receiver 450. Thus, in some embodiments, the transceiver 436 may send data to and receive data from the detachable sensor pods 120, the receiver 450, or devices capable of receiving the sensor data. In another embodiment, more than one radio module 436 may be included in the sensor hub 130, such as a receiver (not shown) for receiving wireless signals from detachable sensor pods 120 and a transceiver 436 configured to communicate with (e.g., send sensor data to and received configuration in command signals from) a receiver 450. When the detachable sensor pods 120 are disconnected from the sensor hub, the wireless transfer of data from the transceivers 426 of the detachable sensor pods 120 to the transceiver 436 and the controller 435 of the sensor hub 130 may be coordinated to manage data transmission collisions multiple detachable sensor pods, such as assigning time intervals or frequency channels to each detachable sensor pod 120 for transmitting sensor data, or other well known communication multiplexing techniques. To accomplish this, the controller 435 may be configured with processor-executable instructions to implement a communication protocol and/or network protocol for managing communications with multiple detachable sensor pods 120.

The sensor hub 130 may include a power element 437, such as a battery and/or an energy storage circuit (e.g., a capacitor or rechargeable battery) coupled to an energy harvesting element 438 (e.g., a photocell). The power element 437 may be of sufficient capacity to power both the components of the sensor hub 130 and of any of the detachable sensor pods 120 to which the sensor hub 130 is electrically attached. The energy harvesting element 438 may be specifically configured to harvest power from a physical or physiological parameter that is also measured by a sensor. Alternatively, the energy harvesting element 438 may include multiple energy harvesting elements configured to harvest energy from a variety of energy sources (e.g., light, heat, movement, etc.). The energy harvesting element 438 may optionally be configured as a sensor element and an energy harvesting element to supplement sensing from the detachable sensor pods 120. The energy harvesting element 438 may be any of a number of known energy harvesting devices or mechanisms that can be used to convert one form of energy into electrical energy that may be stored in the power element 438 for powering the sensor hub 130 and the attached detachable sensor pods 120. In various embodiments, the energy harvesting element 438 and the power element 437 may be combined in a single device or component. The energy harvesting element 438 may also be used as a sensor.

Figure 5:
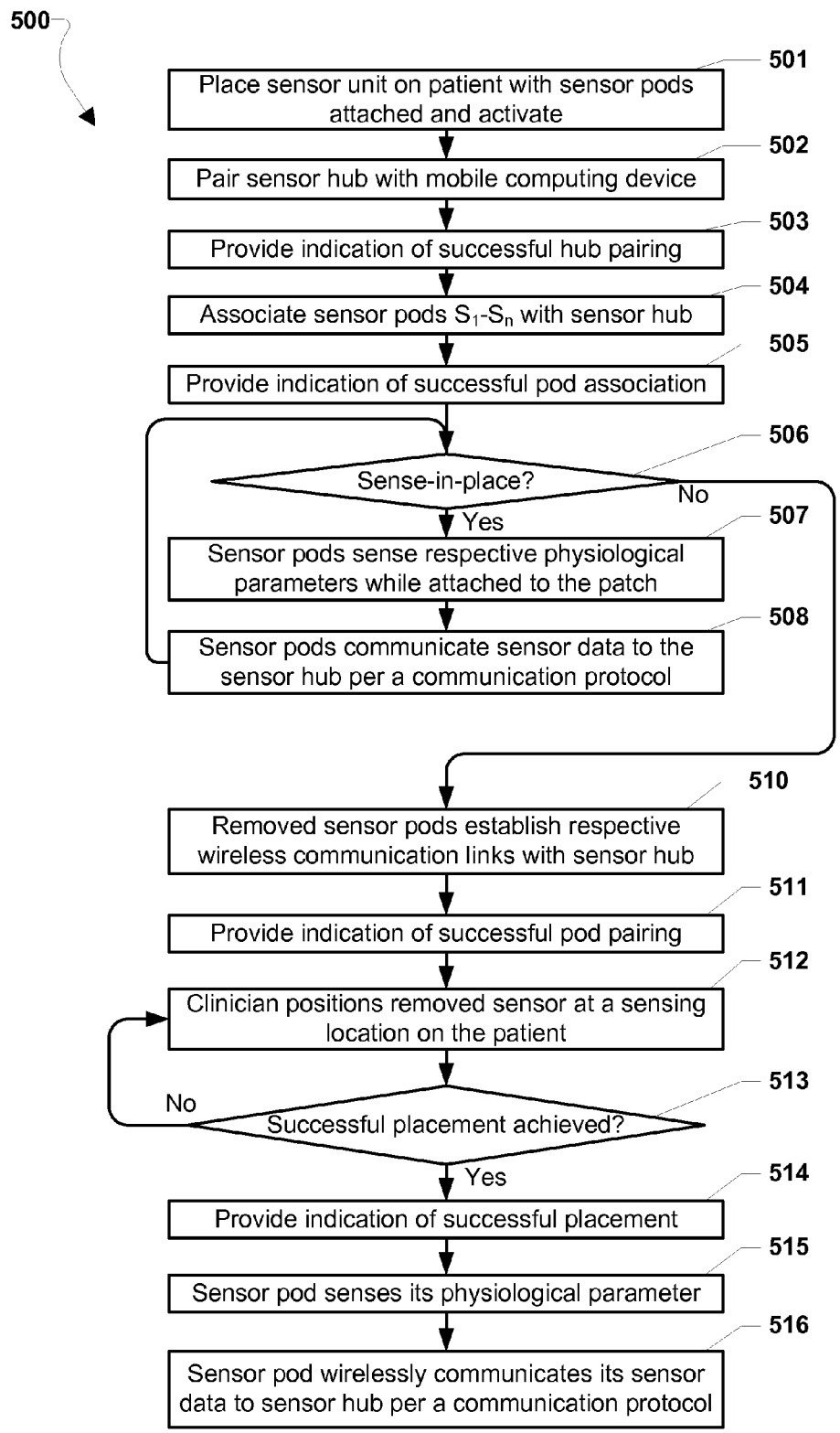
FIG. 5 is a process flow diagram illustrating an embodiment method of sensing quantities with sensor nodes on a sensor hub or removed and positioned.

An embodiment method 500 for placement and operation an integrated adhesive sensor array for sensing for measuring a variety of physical or physiological parameters $Q_1$-$Q_n$ is illustrated in FIG. 5. The embodiment method 500 may be implemented in processor-executable instructions executing on the processors or controllers of the sensor hub and detachable sensor pods, embodiments of which are described above.

The sensor may be placed on an appropriate portion of the body and activated for measurement in block 501. The integrated adhesive sensor array may be affixed to skin of the body using an adhesive backing that at least partially covers a surface of the main sensor unit or patch. In some embodiments, the sensor may be activated, at least in a placement mode, before placement do that a placement-related indication may be provided to assist in proper placement on the body. Alternatively, the integrated adhesive sensor array may be configured to be activated first in a placement mode, and then in an operational or sensor mode. Activation may include removal of a cover film on an adhesive backing on the main sensor unit or patch that functions to activate a power element. For example, one or more terminals of a battery for operating the sensor hub and detachable sensor pods may be covered by a removable insulating layer that is removed along with a film covering the adhesive backing, allowing the terminal to make contact with the sensor hub circuits. Activation of the sensor hub may include a number of initialization operations in block 501 in which executable instructions are loaded into controllers, initial values are set, and self check operations are performed.

In block 502, the sensor hub may initialize and establish a communication link (i.e., pair) with a receiver that is within communication range of the sensor hub. Such pairing with the receiver in block 502 may be accomplished according to known communication protocols, such as a Bluetooth protocol. For example, the sensor hub may monitor for link availability advertisement transmissions from the receiver. Provided that the receiver is recognized by the sensor hub, the sensor hub and the receiver may exchange pairing messages, such as handshaking signals, authentication credentials and encryption keys enabling it to establish a secure communication link suitable for transmitting patient medical data. Because the sensor data may be sensitive or subject to regulations requiring protection of patient information, communications between the sensor hub and the receiver may be encrypted, particularly in embodiments configured for use outside of hospital facilities (e.g., by paramedics and first responders). The communication link established between the receiver and the sensor hub may be managed by an application executing on the receiver. In this way, the sensor hub may be identified to or recognized by the receiver in a registration process that may be performed as part of the operations in block 502. Alternatively, before activating for operation, the sensor may be activated and preconfigured or pre-paired with the receiver to simplify paring for operation.

When the sensor hub is successfully paired with the receiver, an indication that a wireless communication link may be displayed on an indicator or display of the sensor hub in block 503. The indication may be an audible or visual indication, or combination of audible and visual indications, and may include a change in color, a change in sound, an alphanumerical display, and combinations thereof. The displayed indication may also change during a registration process, such as to indicate that pairing has begun, that a registration process is being conducted, and finally that the communication link has been established and use of the sensors may begin.

When detachable sensor pods are positioned on the main sensor unit or patch they may be coupled electrically to the sensor hub through wired connections to receive power and communicate data as described above. When the detachable sensor pods $S_1$-$S_n$ are electrically connected to the sensor hub, an association or communication link may established between the sensor hub and each of the detachable sensor pods $S_1$-$S_n$ in block 504. This association may include initiating a network protocol to manage communications between the sensor hub and the detachable sensor pods to avoid message collisions, such as time-based or frequency-based multiplexing, polling, or other coordination mechanism.

When the detachable sensor pods are successfully associated and communicating with the sensor hub, an indication of successful association may be displayed on the displays or indications of one or both of the sensor hub and the detachable sensor pod indicator in block 505. As discussed above, this indication may be a visual indication, an audible indication, or a combination of visual and audible indications. Visual indications may include a color change, an alphanumeric code or message, or other visual indication. The audible indication may be a beep, a tone, a vibration, or series of tones or vibrations or other audible or tactile indications.

While detachable sensor pods are in place on the main sensor unit or patch in communicating with the sensor hub via electrical connections, the sensors in the detachable sensor pods may sense or measure their respective physical or physiological parameters. That is, when the sensor hub and detachable sensor pods have been activated, the sensors may begin sensing their respective physical or physiological parameters before the detachable sensor pods are removed from the patch and affix to other positions on the patient. Since the communication mechanisms used to send data to the sensor hub differs depending upon whether the detachable sensor pods are deployed or in place on the main sensor unit or patch, the controller in each detachable sensor pod may determine whether it is positioned on the patch and thus configured to sense in place in determination block 506. When each detachable sensor pod controller determines that it is still positioned on the patch and thus sensing in place (i.e., determination block 506="Yes"), the detachable sensor pods may begin taking sensor readings of their respective physical or physiological parameters (e.g., pulse, blood pressure, EKG, etc.) in block 507, and communicate their sensor data via electrical connections to the sensor hub for a communication protocol in block 508. As discussed above, the sensor hub may establish a coordinated communication scheme or communication protocol with the detachable sensor pods in order to facilitate the communication of data and avoid message collisions. Such a protocol may be a time- or frequency-based multiplexing communication scheme, a data polling scheme, or randomized data transmission scheme, to name but a few examples of known communication protocols that may be implemented. For example, in a data polling scheme, the sensor hub may periodically poll each detachable sensor pod in turn to request transmission of its sensor data.

When the controller on a detachable sensor pod determines that it is not on the main sensor unit patch, and thus is not sensing in place (i.e., determination block 506="No"), the detachable sensor pod may establish a wireless communication link with the sensor hub in block 510. The action of removing the detachable sensor pod from the connectors on the docking area may provide a signal or may otherwise create a condition that activates the transceiver on the removed detachable sensor pod. Activation of the detachable sensor pod transceiver may begin a wireless link negotiation process with the sensor hub, such as a Bluetooth pairing negotiation. As discussed above, an indication may be displayed on an indication of the removed detachable sensor pod when it is successfully paired with the sensor hub in block 511. Again, this indication may be visual, audible, or a combination of visual and audible.

As part of establishing a wireless communication link between the sensor hub and each removed detachable sensor pod, the sensor hub and detachable sensor pod may implement a different communication protocol (e.g., a wireless communication protocol) then used for the sense-in-place detachable sensor pods. When the detachable sensor pods are removed from the main sensor unit or patch, coordination of the communications between the removed detachable sensor pods and the sensor hub, and the in-place detachable sensor pods and the sensor hub may become of particular concern. Because the detachable sensor pods are initially connected directly to the sensor hub, the coordination of communications between the detachable sensor pods and the sensor hub may be established using a wired network protocols during this condition. That is, based on the initial direct connection to the sensor hub, the detachable sensor pod may be provided with a clock or other timing signal from the sensor hub as well as information regarding the proper interval or time slots during future which to report its sensor readings to the sensor hub. Thus, when removed the detachable sensor pod may transmit signals at pre-established times. The transmissions may be sent from the detachable sensor pod to the sensor hub with or without acknowledgement by the sensor hub. Because only some of the detachable sensor pods may be removed, a polling scheme may be used to simplify the coordination between the sensor hub and the removed and in-place detachable sensor pods. In such a scheme, the sensor hub may send a signal to the detachable sensor pod, either through the electrical connection with the in place detachable sensor pods, or through a wireless communication link to the detached detachable sensor pods, signaling for the polled detachable sensor pod to transmit its data. In a scheduled polling communication protocol, the detachable sensor pod may be configured to respond to a polling signal within a certain time to preserve the coordination. In an ad-hoc or unscheduled polling configuration, the sensor hub may poll the next detachable sensor pod only after a transmission has been received from the currently polled detachable sensor pod. Given the possibility of a timeout if the currently polled detachable sensor pod fails to respond at all within a prescribed time frame, the sensor hub may proceed if no response is received from the currently polled detachable sensor pod.

Detached sensor pods may be positioned or repositioned on the body at a location for sensing its respective physical or physiological parameter in block 512. The location on the body on which each detachable sensor pod, when detached, is positioned may depend upon the physical or physiological parameter that it measures. For example, a pulse sensing detachable sensor pod may need to be positioned at a location where a pulse can be observed, such as over a vein or in the vicinity of the heart.

As another example, an EKG detachable sensor pod may need to be positioned at a particular location with respect to the patient's heart and chest in order to pick up particular electrophysiology signals. An EKG sensing configuration may involve the placement of several "leads" that are used to sense specific electrophysiology signals associated with monitoring heart activity of a patient. The leads may include limb leads that connect to patient arms and legs, and detect inter-limb voltages. The leads may further include precordial leads that may be connected to the chest of the patient in proximity to the heart. The combination of signals from all of the detachable sensor pods, or leads, may result in an enhanced EKG reading compared to that which would be possible if the detachable sensor pods remained in place.

To facilitate proper placement of detachable sensor pods by clinicians, the detachable sensor pods may be configured with a mechanism for determining whether a proper placement has been achieved. As discussed above, such placement mechanisms may involve use of a body-coordinate system against that each detachable sensor pod can use to compare its location against a stored coordinate value. Another placement mechanism may involve the sensor pod controller sampling sensor data as the detachable sensor pod is applied to the patient and determining whether the target physical or physiological parameter can be sent. Thus, in determination block 513, the controller of a detachable sensor pod may determine whether the detachable sensor pod has been successfully placed on the patient in an appropriate sensing location.

In various embodiments, one or more of the sensor hub, the receiver, or a medical system, may store information regarding the sufficiency of sensor signals from the detachable sensor pods that constitute adequate readings, optimum readings or other levels of sensor signal sufficiency. Alternatively, the sensor hub may simply provide the ability to detect when a certain level is achieved for reception of the sensor reading from the detachable sensor pod. For example, in order for the position to be considered proper or "successful," the sensor signal may need to be at a threshold level or exhibiting a characteristic pattern associated with the desired physical or physiological parameter.

When the sensor pod controller determines that it has been properly positioned on the body (i.e., determination block 513="Yes"), an indication of successful placement may be displayed in block 514. As described above, such an indication may be visual, audible, or a combination of visual and audible indications. As long as that indication of successful placement is not displayed (i.e., determination block 513="No"), a clinician may continue to reposition the detachable sensor pod until a successful placement indication is displayed, such as the sensor pod indication turning green. In an embodiment, an indication may be displayed to inform the clinician when the detachable sensor pod is nearing an optimal position. That is, the indication could display a gradient or relative degree of successful placement using color, intensity, or display element that changes incrementally as the detachable sensor pod approaches or moves farther away from a "successful" placement. For example, the sensor pod indication may turn from red to yellow as the detachable sensor pod approaches an appropriate sensing position on the body. In this manner, feedback provided by the sensor pod indication may help the clinician recognize when the detachable sensor pod has been properly positioned.

When detachable sensor pod has been successfully placed on the body, the detachable sensor pod's sensor begins sensing or measuring its physical or physiological parameter in block 515. In block 516, the detachable sensor pod wirelessly communicate it sensor data to the sensor hub for a communication protocol, such as Bluetooth. The sensing of physical or physiological parameters and communication of sensor data to the sensor hub in blocks 515 and 516 may continue so long as the body monitoring continues and/or power is available to the detachable sensor pods.

Figure 6:
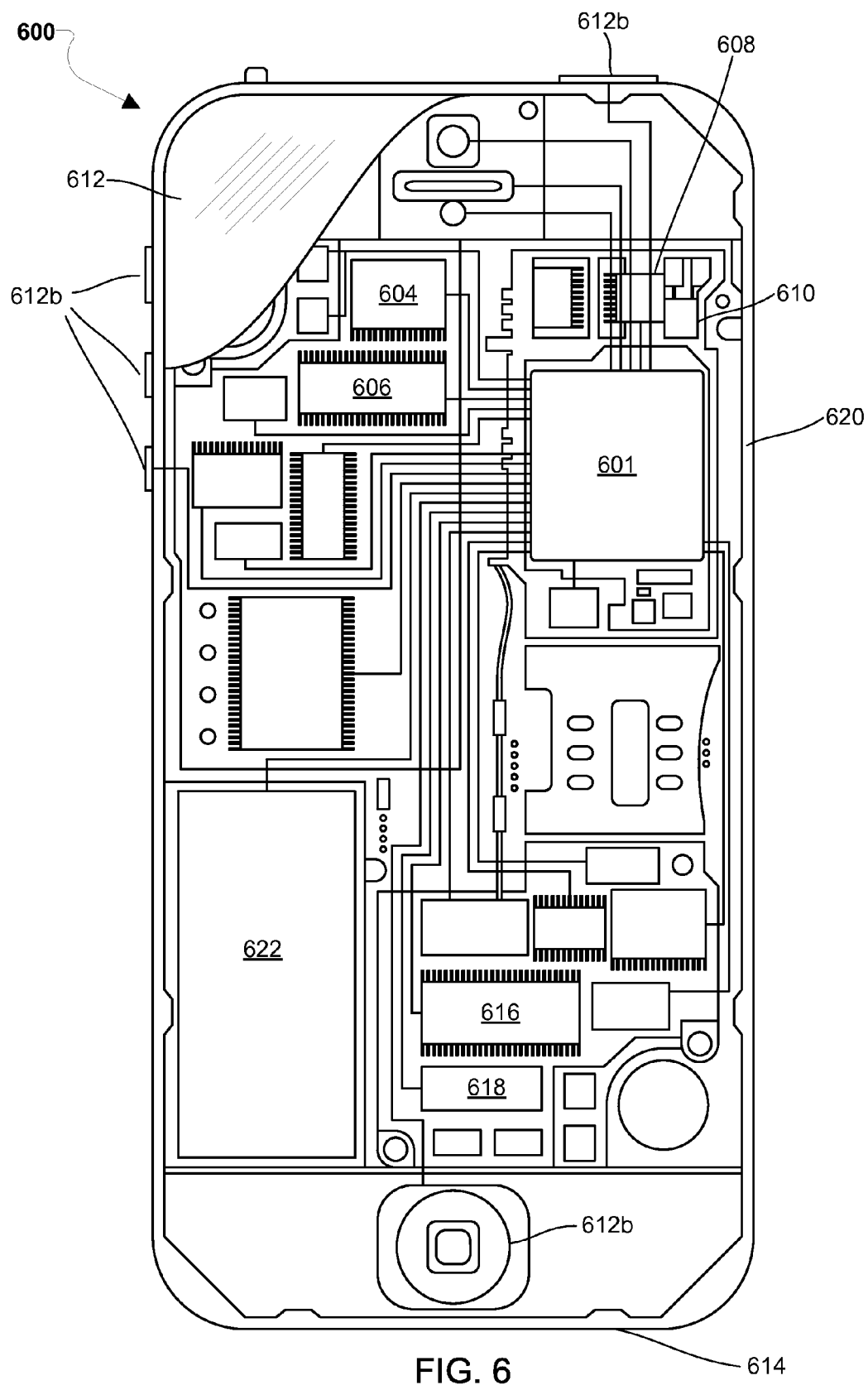
FIG. 6 is a component block diagram illustrating an example mobile device suitable for use with the various embodiments.

The various embodiments may be implemented with a variety of different types of receivers, such as a smart phone a mobile computing device. Typical smart phone mobile computing devices 600 will have in common the components illustrated in FIG. 6. For example, a smart phone mobile computing device 600 may include a processor 601 coupled to internal memories 604 and 606 for storing information. Internal memories 604 and 606 may be volatile or non-volatile memories, and may also be secure and/or encrypted memories, or unsecure and/or unencrypted memories, or any combination thereof. The processor 601 may also be coupled to a touch screen display 612, such as a resistive-sensing touch screen, capacitive-sensing touch screen infrared sensing touch screen, or the like. In some embodiments, the display of the mobile computing devices 600 need not have touch screen capability.

A smart phone mobile computing device 600 may have one or more radio signal transceivers 608 (e.g., Peanut®, Bluetooth®, Zigbee®, Wi-Fi, RF radio) and an antenna 610, or antenna module for coupling to an antenna device, for sending and receiving radio signals. The radio signal transceivers 608 may be coupled to each other and/or to the processor 601. The mobile computing devices 600 may include a cellular network wireless modem chip 616 that enables communication via a cellular data network (e.g., CDMA, TDMA, GSM, PCS, 3G, 4G, LTE, or any other type of cellular data network) and is coupled to the processor 601. The mobile computing devices 600 may include a peripheral device connection interface 618 coupled to the processor 601. The peripheral device connection interface 618 may be singularly configured to accept one type of connection, or multiply configured to accept various types of physical and communication connections, common or proprietary, such as USB, FireWire, Thunderbolt, or PCIe. The peripheral device connection interface 618 may also be coupled to a similarly configured peripheral device connection port. A smart phone mobile computing device 600 may also include a speaker 614, or speakers, for providing audio outputs. A smart phone mobile computing device 600 may also include a housing 620, constructed of a plastic, metal, or a combination of materials, for containing all or some of the components discussed herein. In some embodiments a physical antenna structure may be incorporated into the housing 620 and coupled to the antenna module 610. A smart phone mobile computing device 600 may include a power source 622 coupled to the processor 601, such as a disposable or rechargeable battery. The rechargeable battery may also be coupled to the peripheral device connection port to receive a charging current from a source external to the mobile computing devices 600. A smart phone mobile computing device 600 may also include a GPS receiver coupled to the processor 601 for determining locations of the device. A smart phone mobile computing device 600 may also include physical buttons 612b for receiving user inputs.

Figure 7:
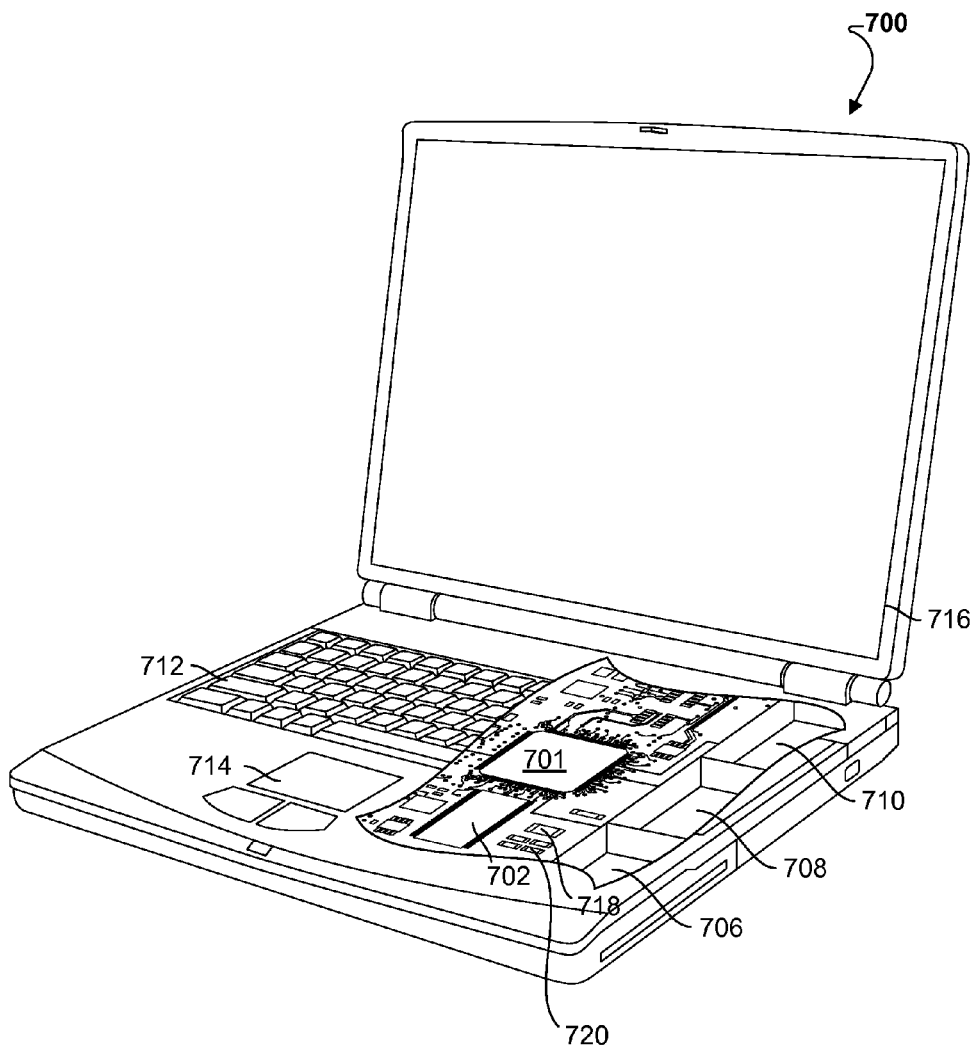
FIG. 7 is a diagram illustrating an example computing device suitable for use with the various embodiments.

The various embodiments described above may also be implemented within and/or with a variety of computing devices for receiving sensor data from a sensor hub, such as a personal computer 700 illustrated in FIG. 7. A personal computer 700 will typically include a processor 701 coupled to volatile memory and a large capacity nonvolatile memory, such as a flash memory device 702. The personal computer 700 may also include a floppy disc drive and a compact disc (CD) drive coupled to the processor 701. A personal computer 700 may also include a number of network transceivers or network connector ports 706 coupled to the processor 701 configured to enable the processor 702 to communicate with other computing devices one or more wired or wireless networks. As a particular example, the network transceivers of a laptop computer 700 may include Ethernet, USB or FireWire® connector sockets/transceivers, one or more wireless modem transceivers, such as Wi-Fi and/or cellular data network transceivers, coupled to one or more antenna for sending and receiving electromagnetic radiation. A personal computer 700 may also include other types of network connection circuits for coupling the processor 701 to a network that may be developed in the future. In a notebook configuration as shown in FIG. 7, the computer housing 705 includes the touchpad 707, the keyboard 708, and the display 709 all coupled to the processor 701. Other configurations of the computing device may include a computer mouse or trackball coupled to the processor (e.g., via a USB input) as are well known, which may also be used in conjunction with the various embodiments.

The processors 601, 701 may be any programmable microprocessor, microcomputer or multiple processor chip or chips that can be configured by software instructions (applications) and transformed into a special purpose processor to perform a variety of functions, including the functions, procedures, algorithms or other processes of the various embodiments described herein. In some mobile devices, multiple processors may be provided, such as one processor dedicated to wireless communication functions and one processor dedicated to running other applications. Typically, software applications may be stored in the internal memory 602, 702 before they are accessed and loaded into the processor 601, 701. The processor 601, 701 may include internal memory sufficient to store the application software instructions and other information.

Those of skill in the art will appreciate that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Further, those of skill in the art will appreciate that the foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

The functions in the various embodiments may be implemented in hardware, software, firmware, or any combination thereof. If implemented in software, the functions may be stored as one or more processor-executable instructions or code on a non-transitory computer-readable medium or non-transitory processor-readable medium. The steps of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the invention. Thus, the present invention is not intended to be limited to the embodiments shown herein but is to be accorded the widest scope consistent with the following claims and the principles and novel features disclosed herein.

What is claimed is:

1. An integrated adhesive sensor array for measuring a physical or physiological parameter of a body, comprising:
   a patch;
   a sensor hub coupled to the patch; and
   a detachable sensor pod detachably coupled to the patch, wherein:
   the patch comprises:
      a flexible adhesive substrate configured to adhere the patch and sensor hub coupled to the patch directly to the body;
      a flexible layer integrated with the flexible adhesive substrate, the flexible layer supporting the sensor hub and sensor hub wiring coupled to the sensor hub; and
      a docking area where the detachable sensor pod is detachably coupled, the docking area including a connector coupled to the sensor hub wiring;
   the sensor hub comprises:
      a wireless transceiver;
      a first energy storage element; and
      a processor coupled to the wireless transceiver, the sensor hub wiring, and the first energy storage element, wherein the processor is configured with processor-executable instructions to perform operations comprising establishing a first wireless communication link with a receiver when the sensor hub is within range of the receiver; and
   the detachable sensor pod comprises:
      a sensor;
      a second energy storage element; and
      a transmitter coupled to the sensor, and the second energy storage element,
      wherein the detachable sensor pod is configured such that:
         the detachable sensor pod is coupled to and is powered by the sensor hub through a connection to the connector coupled to the sensor hub wiring on the patch when the detachable sensor pod is attached to the docking area;
         the detachable sensor pod transmits sensor data to the sensor hub via a second wireless communication link established between the transmitter of the detachable sensor pod and the sensor hub wireless transceiver when the of detachable sensor pod is detached from the docking area.

2. The integrated adhesive sensor array of claim 1, wherein:
the sensor hub further comprises a first indicator coupled to the processor; and
the processor is configured with processor-executable instructions to perform operations comprising providing a first indication on the first indicator when the first wireless communication link is established with a receiver.

3. The integrated adhesive sensor array of claim 2, wherein the processor is configured with processor-executable instructions to perform operations further comprising providing a second indication on the first indicator regarding proper placement of the detachable sensor pod on a body when the detachable sensor pod is detached from the docking area.

4. The integrated adhesive sensor array of claim 3, wherein the first indicator is configured to provide a first version of the second indication when a placement criterion is satisfied and a second version of the second indication when the placement criterion is not satisfied.

5. The integrated adhesive sensor array of claim 4, wherein the first version of the second indication is a green display and the second version of the second indication is a red display.

6. The integrated adhesive sensor array of claim 1, wherein the docking area is disposed on a protrusion of the flexible substrate and the flexible integrated layer configured to enable the integrated sensor array to be affixed to a surface having an irregular contour.

7. The integrated adhesive sensor array of claim 6, wherein the protrusion is further configured to distribute a force generated by removing the detachable sensor pod from the docking area in order to resist tearing.

8. The integrated adhesive sensor array of claim 3, wherein the detachable sensor pod is configured such that the second indication, which is provided on the first indicator regarding proper placement of the detachable sensor pod on a body, is provided by comparing a signal from the sensor of the detachable sensor pod to a threshold value of an acceptable sensor signal and generating the second indication when the sensor signal satisfies the threshold value based on the comparing.

9. The integrated adhesive sensor array of claim 3, wherein the detachable sensor pod further comprises a second indicator and the detachable sensor pod is configured to provide a third indication via the second indicator regarding proper placement of the detachable sensor pod on a body by:
determining a current location of the detachable sensor pod with respect to the body;
comparing the current location of the detachable sensor pod with respect to the body to a proper placement location for the detachable sensor pod; and
providing the third indication via the second indicator based on whether the current location of the detachable sensor pod compares favorably to the proper placement location for the detachable sensor pod.

\* \* \* \* \*